United States Patent
Boyko et al.

(10) Patent No.: US 8,721,621 B2
(45) Date of Patent: May 13, 2014

(54) SYSTEMS AND METHODS FOR DEPLOYING DEVICES TO GENITOURINARY SITES

(75) Inventors: Jim Boyko, Attleboro, MA (US); Grace Kim, Cambridge, MA (US); Heejin Lee, Arlington, MA (US); Michael J. Cima, Winchester, MA (US); Jennie Kwo, Cambridge, MA (US)

(73) Assignee: TARIS Biomedical, Inc., Lexington, MA (US)

( * ) Notice: Subject to any disclaimer, the term of this patent is extended or adjusted under 35 U.S.C. 154(b) by 436 days.

(21) Appl. No.: 12/879,638

(22) Filed: Sep. 10, 2010

(65) Prior Publication Data
US 2011/0202036 A1 Aug. 18, 2011

Related U.S. Application Data

(60) Provisional application No. 61/241,229, filed on Sep. 10, 2009, provisional application No. 61/311,103, filed on Mar. 5, 2010.

(51) Int. Cl.
*A61M 31/00* (2006.01)
*A61M 25/00* (2006.01)

(52) U.S. Cl.
USPC ............ 604/517; 604/57; 604/59; 604/60; 604/275; 604/523

(58) Field of Classification Search
None
See application file for complete search history.

(56) References Cited

U.S. PATENT DOCUMENTS

| | | | |
|---|---|---|---|
| 2,118,631 A * | 5/1938 | Wappler | 604/170.02 |
| 4,955,858 A | 9/1990 | Drews | |
| 6,139,535 A * | 10/2000 | Greelis et al. | 604/500 |
| 6,171,298 B1 | 1/2001 | Matsuura et al. | |
| 6,183,461 B1 | 2/2001 | Matsuura et al. | |
| 6,419,690 B1 * | 7/2002 | Mikus et al. | 607/105 |
| 6,996,433 B2 * | 2/2006 | Burbank et al. | 600/431 |
| 7,066,914 B2 | 6/2006 | Andersen | |
| 7,647,112 B2 | 1/2010 | Tracey et al. | |
| 2003/0015203 A1 | 1/2003 | Makower et al. | |
| 2005/0251108 A1 * | 11/2005 | Frassica | 604/540 |
| 2006/0217656 A1 * | 9/2006 | Freyman et al. | 604/31 |
| 2006/0259118 A1 | 11/2006 | Pal et al. | |
| 2007/0202151 A1 * | 8/2007 | Lee et al. | 424/426 |
| 2008/0119729 A1 * | 5/2008 | Copa et al. | 600/435 |
| 2008/0312636 A1 | 12/2008 | Miller et al. | |
| 2009/0149833 A1 | 6/2009 | Cima et al. | |
| 2010/0003297 A1 | 1/2010 | Tobias et al. | |
| 2010/0152704 A1 | 6/2010 | Lee et al. | |

FOREIGN PATENT DOCUMENTS

| | | |
|---|---|---|
| WO | 2007021964 A2 | 2/2007 |
| WO | 2009076547 A2 | 6/2009 |
| WO | 2010019507 A2 | 2/2010 |

* cited by examiner

*Primary Examiner* — Emily Schmidt
*Assistant Examiner* — Lauren M Peng
(74) *Attorney, Agent, or Firm* — Sutherland Asbill & Brennan LLP

(57) ABSTRACT

A method delivers an implantable device through the urethra and into the bladder. A deployment instrument is inserted into the urethra, the implantable device is inserted into the deployment instrument, and a stream of fluid is injected into the deployment instrument. The stream of fluid drives the implantable device from the deployment instrument into the bladder. The deployment instrument is removed from the urethra, leaving the implantable device wholly implanted in the bladder.

21 Claims, 8 Drawing Sheets

SYSTEMS AND METHODS FOR DEPLOYING DEVICES TO GENITOURINARY SITES

CROSS-REFERENCE TO RELATED APPLICATIONS

The present application claims priority to U.S. Provisional Application No. 61/241,229, which was filed Sep. 10, 2009, and U.S. Provisional Application No. 61/311,103, which was filed Mar. 5, 2010. Both of these applications are incorporated by reference in their entirety.

BACKGROUND

The present disclosure generally relates to systems and methods for deploying medical devices to genitourinary sites, particularly with reference to catheters and stylets for deploying implantable drug delivery devices in the bladder.

A catheter is a device that is positioned in the body to provide ingress and egress to sites within the body. Often, catheters are employed to provide ingress and egress to genitourinary sites within the body, such as the bladder or other locations within urological or reproductive systems. However, known catheters are not suited for deploying implantable devices into the bladder. Some known catheters are designed for the instillation or drainage of fluid, but these catheters often have narrow interior lumens that are not wide enough for passage of an implantable device. Known systems for implanting devices are often designed for passing the device along an exterior of a guidewire, which presents the risk of damage to the device or the body. Further, most known catheters are not suited for deploying devices that are flexible. Particularly, flexible devices may not be able to exit a distal end of many known catheters without getting lodged or wedged in an exit opening.

A need exists for systems and methods for deploying devices to genitourinary sites in the body. More particularly, a need exists for systems and methods for deploying flexible drug delivery devices into the bladder.

SUMMARY

A method delivers an implantable device through the urethra and into the bladder. A deployment instrument is inserted into the urethra, the implantable device is inserted into the deployment instrument, and a stream of fluid is injected into the deployment instrument. The stream of fluid drives the implantable device from the deployment instrument into the bladder. The deployment instrument is removed from the urethra, leaving the implantable device wholly implanted in the bladder.

The implantable device may be loaded into the deployment instrument either before or after the deployment instrument is inserted into the urethra. In embodiments in which the implantable device is loaded into the deployment instrument after the deployment instrument is inserted into the urethra, the implantable device may be loaded into the deployment instrument from its proximal end, and the stream of fluid may drive the implantable device along the length of the deployment instrument and into the bladder.

The stream of fluid may have an equal or higher viscosity than water. For example, a stream of lubricant may be used. The stream of fluid may act on a movable seal positioned downstream of the implantable device, and the movable seal may act on the implantable device to drive the device through the deployment instrument.

To verify placement of a distal end of the instrument in the bladder, urine may be returned through the deployment instrument. Once placement of the distal end of the deployment instrument in the bladder is verified, the return of urine through the deployment instrument may be prevented. An inflatable balloon may be inflated on a distal end of the deployment instrument to anchor the distal end in the bladder. A volume of fluid may be delivered through the deployment instrument into the bladder before the implantable device is implanted, forming a cushion for the implantable device in the bladder. Once the implantable device has been deployed, a stylet may be driven through the deployment instrument to verify the implantable device was driven into the bladder.

In another embodiment, a kit or package includes a deployment instrument and an implantable medical device. The deployment instrument includes a number of lumens, one of which is a deployment lumen that has the implantable medical device pre-loaded therein. The implantable medical device may be a flexible drug delivery device, which may be configurable between a retention shape and a deployment shape. The deployment instrument may include a urine return lumen, which is in communication with a urine entry opening on a distal end portion of the deployment instrument and a urine return port on a proximal end of the deployment instrument. The deployment instrument also may include a solid distal tip, the deployment lumen curving toward a side of the deployment instrument adjacent to the solid distal tip and the deployment lumen terminating in an exit opening formed through a side of the deployment instrument. The deployment instrument may include a plunger and a handle operatively connected to the plunger. The distal end portion of the deployment instrument may include an inflatable balloon, and at least one of the lumens may be in fluid communication with the inflatable balloon. The kit may include a syringe. The syringe may be connectable to a proximal end of the deployment instrument to deliver a volume of a fluid into the deployment instrument. The volume of fluid may drive the implantable medical device from the deployment instrument. Also in some embodiments, the kit may include a stylet. The stylet is insertable into a proximal end of the deployment instrument. The stylet is suitable for driving the implantable medical device from the deployment instrument.

A deployment device can deliver an implantable device into a bladder. The deployment device includes a sidewall that is sized to reach through the urethra to the bladder. The sidewall defines a deployment lumen that is sized and shaped for housing the implantable device. A solid tip is positioned at a distal end of the sidewall, and an exit opening is formed in the sidewall adjacent to the solid tip. The exit opening is in fluid communication with the deployment lumen, which curves toward the exit opening so that the distal tip is solid. The exit opening may be off center from a longitudinal axis of the deployment lumen. A proximal end portion of the deployment instrument may be configured to sealably connect to a syringe for delivering a driving fluid into the deployment lumen, and a urine return lumen may be provided for returning urine from the bladder to indicate placement of the distal tip in the bladder.

A system for implanting a drug delivery device through the urethra into the bladder includes a deployment catheter and a fluid introduction mechanism. The deployment catheter is sized to extend through the urethra to the bladder and is pre-loaded with the drug delivery device. The fluid introduction mechanism is associated with the deployment catheter and is operable to inject a fluid into the deployment catheter to drive the drug delivery device into the bladder. The deployment catheter may include a proximal port, and the fluid introduction mechanism may include a syringe removably associated with the proximal port. A movable plug may be positioned in the deployment catheter between the fluid introduction mechanism and the drug delivery device. The fluid may act on the movable plug, and the movable plug may transfer the driving force of the fluid to the drug delivery device.

A system for deploying an implantable device to an implantation site within a body includes a deployment catheter and a stylet. The deployment catheter includes a reinforced tip and is configured for traversing natural lumens of the body to reach the implantation site. The stylet is configured for pushing the drug delivery device out of the catheter. In particular, the catheter may include a substantially solid, rounded distal end, an exit opening formed through a side of the catheter on a proximal side of the distal end, and an interior passageway that curves to terminate at the exit opening.

A method deploys an implantable device into an implantation site. A deployment instrument is inserted into a natural lumen of the body to reach the implantation site. The deployment instrument includes a reinforced tip. The implantable device is introduced into the deployment instrument and is driven through the deployment instrument using a stylet. The stylet includes a central body portion and a distal tip portion. The central body portion has a smaller cross-sectional area than an inner lumen of the deployment instrument, and the distal tip portion has a cross-sectional area that is about the same as the inner lumen of the deployment instrument.

DETAILED DESCRIPTION

Described below are embodiments of systems and methods for deploying an implantable medical device into an implantation site of a body. In particular embodiments, the systems and methods deploy an implantable medical device through one or more natural lumens of the body, such as the urethra, into a genitourinary site of a body, such as the bladder. The systems and methods facilitate wholly implanting an implantable medical device in the body, and the implanted device may remain in the body long after the deployment system has been removed or the deployment method has ended. For example, the implanted device may be a drug delivery device that releases drug into the body over an extended implantation period. The drug delivery device may be implanted in the bladder, free-floating within the bladder and releasing one or more drugs over an extended time period.

In some embodiments, a deployment system is provided. The deployment system generally includes a deployment instrument, such as a catheter, that can be used to deploy an implantable device through the urethra into the bladder or another genitourinary site. The deployment instrument may be specially configured for navigating the urethra to the bladder.

In other embodiments, a deployment method is provided. The deployment method may include deploying an implantable device through a deployment instrument positioned in a natural lumen of the body, such as the urethra, into a body cavity such as the bladder. The implantable device may be driven through the deployment instrument using a flow of fluid or a stylet. The deployment instrument is subsequently removed from the body, leaving the implantable device wholly implanted in the bladder or other genitourinary site. For the purposes of this disclosure, the term genitourinary site refers to any location within a urological or reproductive system of the body, such as a bladder, kidney, urethra, ureter, penis, testicle, seminal vesicle, vas deferens, ejaculatory duct, prostate, vagina, uterus, ovary, or fallopian tube, among others or combinations thereof. However, the implantation site may be any location in the body of a human or animal, whether male or female, adult or child.

Figure 1:
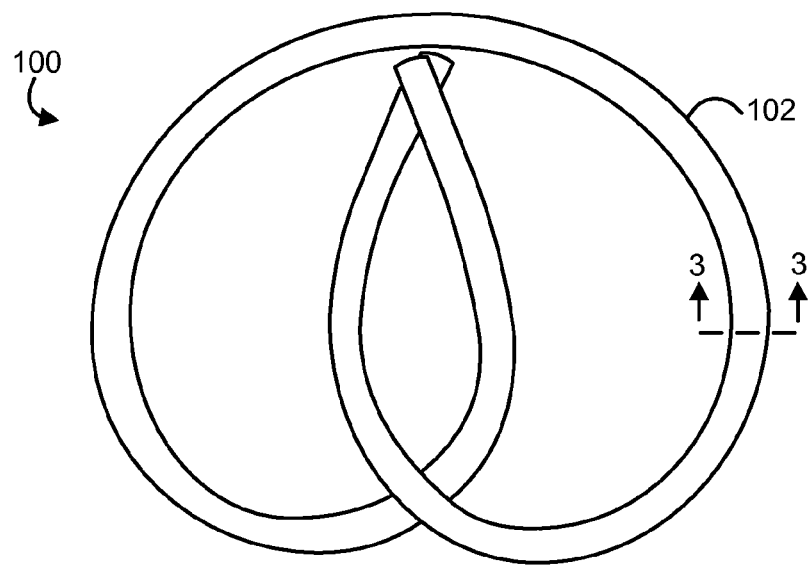
FIG. 1 is a plan view of an embodiment of a drug delivery device.
Figure 2:
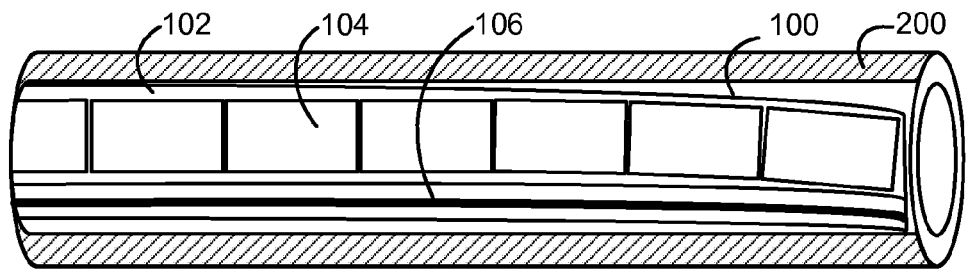
FIG. 2 is a cross-sectional plan view of the drug delivery device shown in FIG. 1, illustrating the drug delivery device inside a deployment instrument.

The deployment systems and methods can be used to implant a wide range of medical devices into the body. In a preferred embodiment, the implantable device is a drug delivery device suited for releasing one or more drugs into the body. One example of such a drug delivery device 100 is shown in FIG. 1, which is designed for implantation in the bladder. In particular, the drug delivery device 100 generally has a retention shape suited for retaining the device in the body, such as in the bladder. The retention shape may be the illustrated pretzel shape, although other shapes can be used. The device 100 also has a flexibility that permits deforming the device 100 into a deployment shape suited for inserting the device 100 through a deployment instrument. For example, the device 100 may assume an elongated or linear shape when positioned within a working channel of a deployment catheter 200, as shown in FIG. 2.

Figure 3:
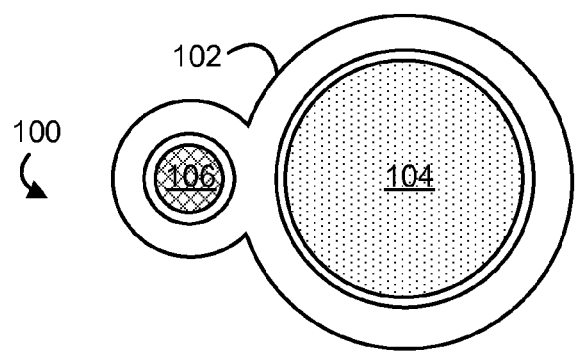
FIG. 3 is a cross-sectional view of the drug delivery device shown in FIG. 1, taken along line 3-3.

As shown in FIG. 3, which is a cross-sectional view of the drug delivery device 100 taken along line 3-3 in FIG. 1, the illustrated device 100 has a device body 102 that defines two internal lumens, which are aligned along their length. One of the lumens houses a drug payload 104, while the other lumen houses a retention frame 106. The walls of the device body 102, which define the lumens, are formed from flexible and/or elastic materials, such as silicone. The retention frame 106 is likewise formed from flexible and/or elastic materials, such as nitinol. The drug payload 104 also may be in a relatively flexible form, such as in the form of a number of discrete solid drug tablets having breaks or interstices formed between them, as shown in FIG. 2. Thus, the device 100 has a flexibility that permits deforming the device between a retention shape as shown in FIG. 1 and a deployment shape as shown in FIG. 2.

Figure 4:
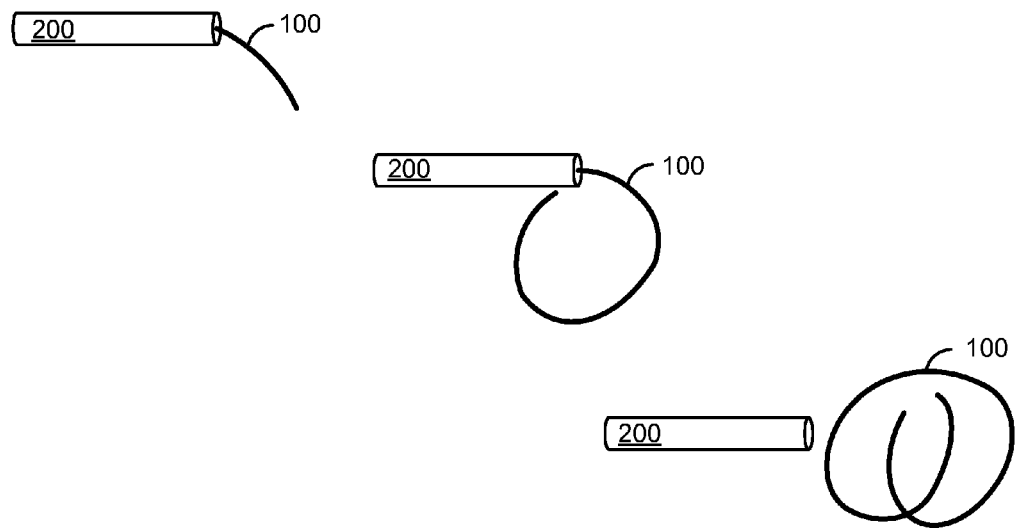
FIG. 4 is a plan view of a portion of a deployment instrument, illustrating the drug delivery device exiting a distal end of the deployment instrument.

In some embodiments, the device 100 naturally assumes the retention shape, but can be deformed into the deployment shape for implantation. Once in the deployment shape, the device can be passed through the deployment instrument 200. The walls of the deployment instrument 200 exert a force on the device 100 that retains the device in the deployment shape. As the device 100 exits the deployment instrument 200, the force is removed and the device 100 returns to the retention shape for retention in the body. An example is shown in FIG. 4, which illustrates the device 100 returning to the retention shape as the device is deployed from the deployment instrument 200. However, the device may be manually adjusted between the retention shape and the deployment shape, such as through the use of a medical instrument. Additional embodiments of this and other drug delivery devices are described in the following U.S. patent applications, which are incorporated by reference herein: U.S. application Ser. No. 11/463,956, filed Aug. 11, 2006; U.S. application Ser. No. 12/333,182, filed Dec. 11, 2008; U.S. application Ser. No. 12/538,580, filed Aug. 10, 2009; U.S. application Ser. No. 12/825,215, filed Jun. 28, 2010; U.S. application Ser. No. 12/825,238, filed Jun. 28, 2010; U.S. application Ser. No. 12/851,494, filed Aug. 5, 2010; U.S. application Ser. No. 12/870,261, filed Aug. 27, 2010; U.S. Provisional Application No. 61/241,229, filed Sep. 10, 2009; U.S. Provisional Application No. 61/267,518, filed Dec. 8, 2009; U.S. Provisional Application No. 61/287,649, filed Dec. 17, 2009; U.S. Provisional Application No. 61/325,713, filed Apr. 19, 2010; U.S. Provisional Application No. 61/311,103, filed Mar. 5, 2010; U.S. Provisional Application No. 61/370,902, filed Aug. 5, 2010; and U.S. Provisional Application No. 61/371,139, filed Aug. 5, 2010.

Figure 5:
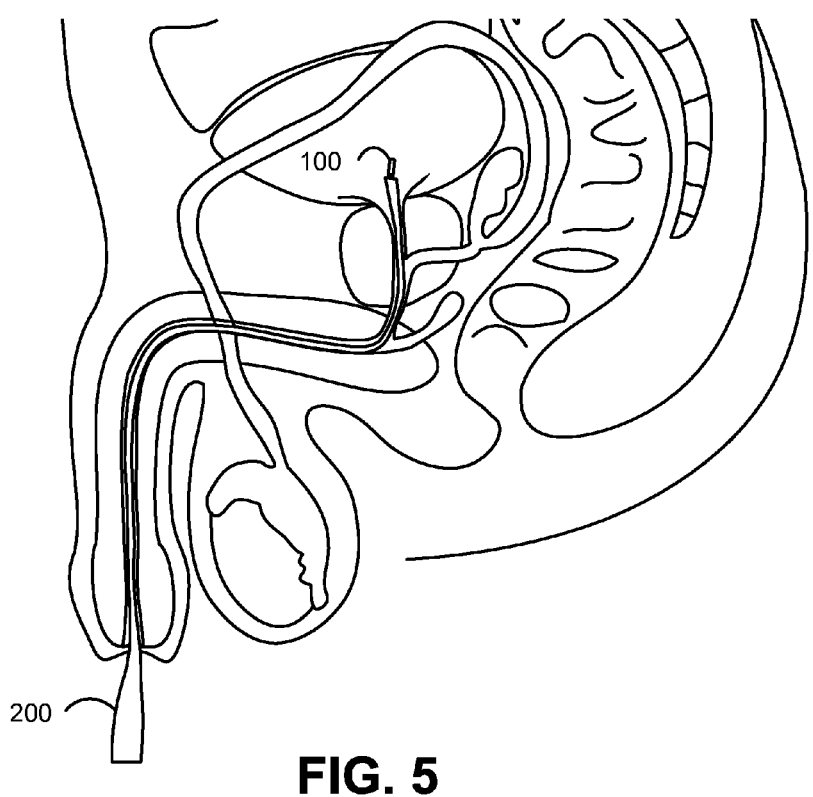
FIG. 5 is a sagittal view of a male genitourinary system, illustrating the drug delivery device being deployed through the urethra into the bladder.

The deployment systems and methods described below can be used to deliver the drug delivery device 100 into a genitourinary site of the body, such as the bladder. An example is shown in FIG. 5, which illustrates the device 100 being deployed from the deployment instrument 200 into the bladder. The deployment instrument 200 is sized and shaped for passing through the urethra to the bladder as shown in FIG. 5, wherein the male anatomy is shown in by way of example. The drug delivery device 100 can be released from the deployment instrument 200 into the bladder, and once implanted the device 100 releases drug into the bladder for an extended period. However, the deployment systems and methods disclosed herein can be used to implant other devices into the body, or alternatively, to provide access into the body for reasons other than the implantation of a device.

Figure 6:
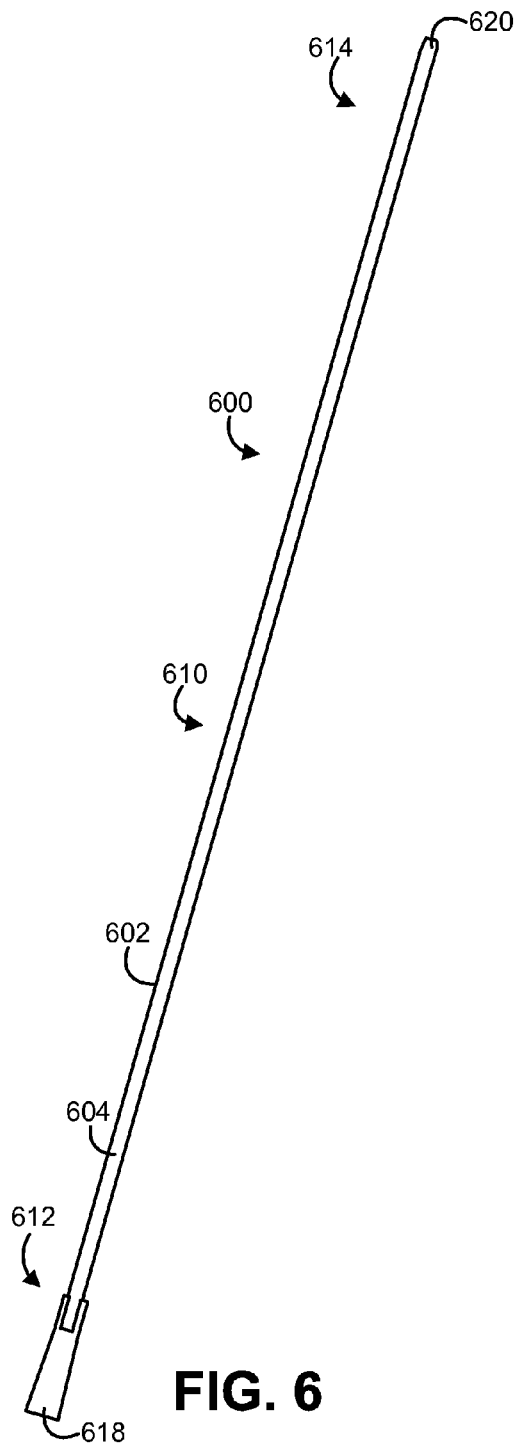
FIG. 6 is a plan view of an embodiment of a deployment instrument.

Embodiments of deployment systems are shown in FIGS. 6 though 31. Generally, the deployment systems include a deployment instrument that is designed to navigate natural lumens of the body to reach an implantation site. The deployment instrument is relatively flexible, which permits inserting the instrument through tortuous pathways of the body to the implantation site, and yet the deployment instrument has sufficient column strength to impede or prevent buckling as the deployment instrument is pushed forward. In some cases, the configuration of the deployment instrument may vary to compensate for differences between male and female anatomy. For example, the instrument may be longer and more compliant for use with male patients, or shorter and semi-rigid for use with female patients. In particular embodiments, the deployment instrument may be a catheter or a portion of another medical device.

The deployment instrument generally includes a central body portion, a proximal end portion, and a distal end portion. The central body portion is configured for extending through natural lumens of the body to the implantation site. For example, the central body portion may be sized and shaped for passing through the urethra to the bladder. The distal end portion is configured for traversing the natural lumens to reach the implantation site. In particular, the distal end portion is strong enough to permit driving the deployment instrument through the natural lumens of the body without buckling or jamming, and yet is flexible enough to minimize or avoid damaging the tissue lumen walls. For example, the distal end portion may traverse the urethra without damaging its walls. The proximal end portion remains outside of the body, providing access for a user, such as a medical professional, or an interface for equipment, such as medical equipment. The deployment instrument also includes at least one internal passageway or lumen extending along its longitudinal length that permits passing a device through the interior of the instrument, so that the device is protected during the implantation procedure.

In addition to permitting passage of the device, the internal passageway may serve other purposes. In some embodiments, the internal passageway may provide a path for fluid to travel through the instrument. For example, lubricant or another suitable fluid may be driven through the internal passageway to drive the device from the internal passageway into the body. As another example, water or another suitable fluid may be delivered through the internal passageway before the device is implanted to form a cushion in the bladder for receiving the device, impeding the device from contacting the bladder wall once implanted. Water also may be directed through the internal passageway to a Foley balloon on a distal end of the instrument for the purpose of inflating the Foley balloon. The internal passageway also may return urine from the bladder to verify the instrument has reached the bladder. In some cases, the deployment instrument includes mechanics operable to eject the drug delivery device from the instrument or to retrieve a previously deployed device back into the instrument, and these mechanics may be housed in the internal passageway. Any number of internal passageways or lumens can be provided, with each lumen being useful for one or a combination of the purposes described above. For example, the deployment instrument may include a main lumen that is used to deliver the drug delivery device into the bladder, a smaller urine return lumen that is used to verify placement of the deployment instrument distal tip in the bladder, and a separate Foley balloon inflation lumen that is in direct fluid communication with the interior of a Foley balloon.

Each internal passageway may extend from a proximal opening on the proximal end portion of the deployment instrument to an distal opening on the distal end portion for the deployment instrument. The distal openings may have various placements or sizes along the distal end portion depending on their purpose, as described below. For example, a urine return opening in communication with a urine return lumen may be spaced downward from the distal-most tip of the deployment instrument by a selected distance, so that urine only passes into the urine return lumen once the distal tip of the deployment instrument is positioned at least the selected distance in the bladder.

At least one exit opening in communication with the internal passageway permits releasing the device from the internal passageway into the bladder or other implantation site. In embodiments, the exit opening is configured to facilitate smooth passage of the device from the interior passageway through the exit opening.

In embodiments, the distal end portion includes one or more of a coude tip, a council tip, and an inflatable balloon. A coude tip may be useful for traversing tortuous pathways through the anatomy, such as near the prostate gland in male patients. A council tip may be useful for inserting the catheter over a guidewire. An inflatable balloon may be inflated to retain the distal end portion of the catheter in the bladder. These distal tip configurations can be used alone or in combination. For example, the use of both a coude tip and inflatable balloon may be especially useful with male patients due to the structure of the male anatomy.

In some embodiments, the proximal end portion is associated with a handle. The handle may be grasped by the user to hold the deployment instrument. In some embodiments, the handle can be actuated by a user to eject the drug delivery device from the catheter, as described below. In other embodiments, the proximal end portion is associated with a luer connector that facilitates forming a relatively water-tight connection between the deployment instrument and an external fluid source, such as a syringe, to introduce fluid into the deployment instrument. The fluid may drive the device toward the implantation site or the fluid may form a cushion in the implantation site for receiving the device, as described below.

The proximal end portion may also have one or more ports, each of which may be in communication with one or more internal passageways or lumens through the deployment instrument. For example, a urine return port may be in communication with a urine return lumen through the catheter, which directs urine from the bladder. As another example, a fluid introduction port may be in communication with a Foley balloon at a distal end of the catheter by way of another separate lumen, so that fluid from outside of the body can be directed to the Foley balloon to inflate it. More than one port may be in communication with any an internal passageway. In some embodiments, any one of the ports may be associated with a valve that permits or prevents the flow of fluid through the port. For example, a valve on a urine return port may be opened so that urine can return through the port to verify placement of the distal tip in the bladder, and thereafter the valve may be closed to prevent the continued return of urine through the urine return port during the implantation process. Alternatively, one valve may be associated with the deployment instrument upstream of a number of ports, so that fluid flow between the deployment instrument and all of the ports can be controlled by opening or closing one valve. Examples of such configurations are described in further detail below.

The dimensions of the instrument are selected based at least in part on the dimensions of the anatomy that the deployment instrument is designed to navigate. In embodiments in which the instrument extends through the urethra to the bladder, for example, the central body portion may have a length in the range of about 30 cm to about 45 cm and an outer diameter in the range of about 3 mm to about 7 mm. An inner diameter of the central body portion is selected based at least in part on the dimensions of the device that the instrument is designed to implant. For example, the instrument can be used to implant an embodiment of the drug delivery device 100 shown in FIG. 1, in which case the inner diameter of the central body portion may be in the range of about 2 mm to about 5 mm. The outer diameter of the instrument is dimensioned to pass through the urethra. For example, the outer diameter may be in the range of about 12 to 18 Fr. In some embodiments, the outer diameter is selected to compensate for differences in the male and female anatomy, with a male version of the deployment instrument having a relatively wider outer diameter than a female version of the deployment instrument. For example, the male instrument may have an outer diameter in the range of about 14 to 18 Fr, such as about 16 Fr, while the female instrument may have an outer diameter in the range of about 12 to 16 FR, such as about 14 Fr. The stiffness of the deployment instrument also may vary according to the anatomy that the deployment instrument is designed to navigate. For example, an embodiment of the deployment instrument suited for navigating the tortuous urethra of the male anatomy may have a thicker wall than an embodiment of the deployment instrument suited for navigating the urethra of the female anatomy.

The wall of the instrument may be relatively thin so that the inner diameter of the instrument is relatively large given the outer diameter of the instrument. Thus, the diameter of the lumen through the instrument may relatively large in view of the overall size of the instrument as a whole. The wall is formed partially or fully from a material that has a column strength suited to prevent buckling despite its thin nature, yet has a flexibility suited for navigating tortuous pathways through natural body lumens such as the urethra. The material also is biocompatible and is compatible with materials used to form the device to be implanted. The material is also amenable to suitable sterilization processes.

One example material that can be used for the deployment instrument is medical grade polyvinyl chloride (PVC). The PVC may be stabilized to permit sterilization with gamma irradiation, which may permit sterilizing the deployment instrument and device together. Other suitable materials include polyethylene (PE), polytetrafluoroethylene (PTFE), styrenic thermoplastic elastomer (STE), silicone, latex rubber, polyurethane, Silitek®, C-flex®, Percuflex®, Tecoflex®, or combinations thereof. In embodiments, the material may be a polymer or copolymer whose composition may be modified or properties enhanced to yield the desired column strength. The deployment instrument can be formed by extrusion, injection molding, or other manufacturing processes known in the art.

The deployment instrument may have markings along its length, such as graduated markings that indicate dimensions or relative positions. The markings may facilitate deploying the deployment instrument in the urethra and determining when the deployment instrument has become properly positioned therein. However, the markings are not necessary.

The implantable device can be loaded into the deployment instrument, through either the exit opening on the distal end portion, through an entry opening on the proximal end portion, or through a slit along the central body portion. The loading location may depend whether the device is loaded into the deployment instrument before or after the deployment instrument is positioned in the body. The loading location also may depend on how the device is ejected from the deployment instrument into the bladder.

Figure 7:
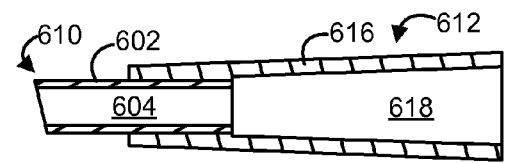
FIG. 7 is a cross-sectional plan view of a proximal end portion of the embodiment of a deployment instrument shown in FIG. 6.
Figure 8:
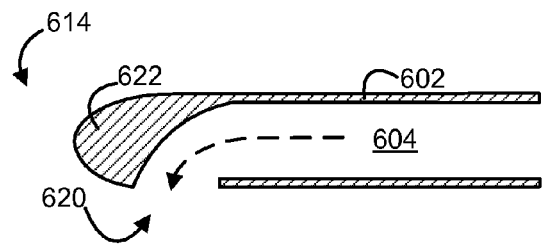
FIG. 8 is a cross-sectional plan view of a distal end portion of the embodiment of a deployment instrument shown in FIG. 6.

FIG. 6 illustrates an embodiment of a deployment instrument 600 that is suited for implanting a drug delivery device or other implantable device in the bladder. The deployment instrument 600 is generally a catheter or a tube having a wall 602 that defines an interior passageway 604, a portion of which is shown in FIGS. 7 and 8. The interior passageway 604 permits passing a device through the interior of the deployment instrument 600, so that the device is protected during the implantation procedure. The wall 602 of the deployment instrument 600 is relatively thin, so that the interior passageway 604 is relatively wide in view of the overall width of the deployment instrument 600. Thus, a relatively larger device can be inserted through a relatively smaller interior passageway 604. The wall 602 is relatively flexible, which permits inserting the deployment instrument 600 through tortuous pathways of the body to the implantation site, and yet the wall 602 has sufficient column strength to impede or prevent the deployment instrument 600 from buckling as the catheter is pushed forward. In embodiments, at least a portion of the wall 602 can be reinforced to improve the kink resistance and rigidity of the deployment instrument 600. For example, the wall 602 may have a reinforcing material embedded on at least a portion of its interior or applied about at least a portion of its exterior. The reinforcing material can be a steel wire or ribbon that is braided, wound, or wrapped about the exterior. The wire or ribbon can be encapsulated within a polymer layer that is applied about the exterior of the deployment instrument 600, such as by coating or re-extruding the deployment instrument with the polymer. Other reinforcing materials also can be used. In the illustrated embodiment, the deployment instrument 600 is a hollow cylindrical tube, although other shapes, such as shapes having oval or elliptical cross-sections, are possible. For example, the cross-sectional shape of the tube may match the cross-sectional shape of the implantable device.

More particularly, the deployment instrument 600 includes a central body portion 610, a proximal end portion 612, and a distal end portion 614. The central body portion 610 is sized for extending through natural lumens of the body to the implantation site. For example, the central body portion 610 may be sized and shaped for passing through the urethra to the bladder. The distal end portion 614 is configured for traversing the natural lumens to reach the implantation site without causing damage or trauma to the body. For example, the distal end portion 614 may traverse the urethra without damaging its walls. The proximal end portion 612 remains outside of the body, providing access for a user, such as a medical professional, or an interface for equipment, such as medical equipment.

The dimensions of the deployment instrument 600 are selected based at least in part on the dimensions of the anatomy that the deployment instrument 600 is designed to navigate. In embodiments in which the deployment instrument 600 extends through the urethra to the bladder, for example, the central body portion 610 may have a length in the range of about 30 cm to about 45 cm and an outer diameter in the range of about 3 mm to about 7 mm. An inner diameter of the central body portion 610 is selected based at least in part on the dimensions of the device that the deployment instrument 600 is designed to implant. For example, the deployment instrument 600 can be used to implant an embodiment of the drug delivery device 100 shown in FIG. 1, in which case the inner diameter of the central body portion 610 may be in the range of about 2 mm to about 5 mm. Thus, the wall 602 of the central body portion 610 is relatively thin. However, the wall 602 is formed from a material that has a column strength suited to prevent buckling despite its thin nature, yet has a flexibility suited for navigating tortuous pathways through natural body lumens such as the urethra. The material also is biocompatible and with materials used to form the device and/or the stylet. The material is also amenable to suitable sterilization processes.

FIG. 7 illustrates the proximal end portion 612 of the deployment instrument 600 in greater detail. The proximal end portion 612 is suited for interfacing with a user or equipment. In some embodiments, the proximal end portion 612 includes a handle 616 that can be grasped by a user. The handle can be integrally formed with the deployment instrument 600, or the handle can be attached separately, such as by bonding. The proximal end portion 612 also can be configured for receiving the device, a stylet, or a flow of liquid, as described below. For example, the proximal end portion 612 can have an entry opening 618 that permits inserting the device, stylet, or a fluid source into the deployment instrument 612. The entry opening 618 may be relatively wider than the interior passageway 604, and extending away from the entry opening 618, the interior passageway 604 may taper. The wider entry opening 618 facilitates easy insertion of the device, the stylet, or the fluid source.

In other embodiments, the proximal end portion 612 is associated with a luer connector. The luer connector facilitates forming a relatively water-tight connection between the deployment instrument 600 and an external fluid source, such as a syringe. Such a configuration is useful in cases in which fluid is introduced into the deployment instrument 600 to drive the device toward the implantation site, as described below.

FIG. 8 illustrates the distal end portion 614 of the deployment instrument 600 in greater detail. The distal end portion 614 includes at least one exit opening 620 that permits releasing the device into the implantation site, such as the bladder. The exit opening 620 is in communication with the interior passageway 604 through the deployment instrument 600 in a manner that facilitates smooth passage of the device from the interior passageway 604 through the exit opening 620. Because the distal end portion 614 leads during insertion of the deployment instrument 600, the distal end portion 614 is configured to navigate tortuous pathways through the body.

The distal end portion 614 is strong enough to permit driving the deployment instrument 600 through the natural lumens of the body without buckling or jamming, and yet is flexible enough to minimize or avoid damaging the tissue lumen walls. For example, the distal end portion 614 may facilitate driving the deployment instrument 600 through the urethra to the bladder.

In particular, the distal tip portion 614 includes a substantially solid distal end 622. The solid distal end 622 facilitates driving the catheter forward without buckling. So that the distal end 622 is solid, the interior passageway 604 stops short of the distal end 622. More particularly, the interior passageway 604 curves toward a side of the deployment instrument and terminates at the exit opening 620, which is formed on the side of the distal tip portion 614 through the wall 602. The curvature of the interior passageway 604 guides the device out of the deployment instrument 600 through the exit opening 620. The distal end 622 also has a rounded exterior surface that facilitates driving the deployment instrument forward without causing trauma to the surrounding anatomy, such as the walls of the urethra. Below the rounded exterior surface, the solid distal end 622 may be integrally formed with the deployment instrument 600 from a single material or may be reinforced or filled with one or more reinforcing materials. A reinforced material also may be positioned about the rounded exterior surface of the distal end 622. In the illustrated embodiment, the exit opening 620 is positioned rearward of the rounded exterior surface, although the exit opening 620 may be at least partially positioned on the rounded exterior surface in some embodiments.

The distal tip portion 614 can be formed in a variety of manners. For example, the distal tip portion 614 can be molded or extruded. In one embodiment, the distal tip portion is overmolded onto the catheter. In some embodiments, the distal tip portion 614 can be an integral portion of the catheter, while in other embodiments, the distal tip portion 614 can be a separate, reinforced tip that is attached to the central body portion 610 of the deployment instrument 600.

Figure 9:
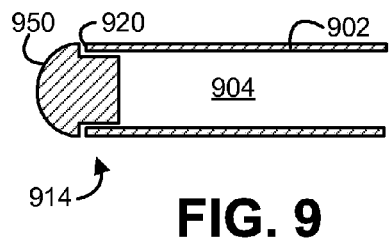
FIG. 9 is a cross-sectional plan view of another embodiment of a distal end portion for a deployment instrument.

The distal tip portion 614 of the deployment instrument 600 can have other configurations, embodiments of which are shown in FIGS. 9-12. FIG. 9 is a cross-sectional plan view of another embodiment of a distal tip portion 914 that is suited for driving the deployment instrument forward through the urethra, yet permits passing the implantable device into the bladder. As shown, a cap member 950 is removably attached to the distal tip portion 914. The cap member 950 is inserted into the interior passageway 904 to close the exit opening 920, which is formed through a distal end of the wall 902. The cap member 950 includes a distal exterior side that is exposed on an outside of the deployment instrument, and a proximal interior side that is positioned in the interior passageway 904. The cap member 950 may be rounded on its distal exterior side. The rounded exterior surface facilitates driving the deployment instrument forward without causing trauma. Between the exterior surface and the interior surface the cap member 950 has a substantially solid body. The body impedes buckling of the deployment instrument as it is driven through the urethra. On its proximal interior side, the cap member 950 is sized and shaped to mate with and close the exit opening 920 and an adjacent portion of the interior passageway 904. The cap member 950 is removably associated with the exit opening 920 so that the cap member 950 can be removed during the implantation procedure, permitting the device to pass through the exit opening 920. For example, as the device is pushed through the interior passageway 904 toward the exit opening 920, the device may forcibly release the cap member 950 from the deployment instrument. In some embodiments, the cap member 950 is formed from a bioerodible or resorbable material, so that the cap member 950 naturally degrades after release into the body. Examples of materials that are suitably strong yet resorbable include poly(glycerol sebacate) (PGS), poly(lactide-co-glycolide) (PLGA), poly(glycolic acid) (PGA), poly(lactic acid) (PLA) and collagen. In other embodiments, the cap member 950 may be tethered to the deployment instrument, so that the cap member 950 is removed from the body upon removal of the deployment instrument.

Figure 10:
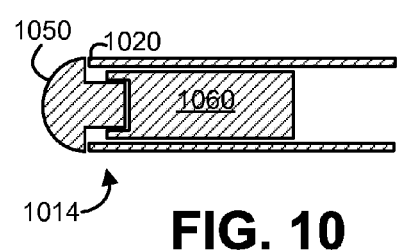
FIG. 10 is a cross-sectional plan view of an additional embodiment of a distal end portion for a deployment instrument.

FIG. 10 is a cross-sectional plan view of yet another embodiment of a deployment instrument distal tip portion 1014. Like the embodiment shown in FIG. 9, the distal tip portion 1014 includes a cap member 1050. The cap member 1050 may be substantially solid and has a rounded exterior surface on its distal exterior side, which facilitates insertion without buckling or trauma. On its proximal interior side, the cap member 1050 is sized and shaped to mate with and close the exit opening 1020, the cap member 1050 being removably associated with the exit opening 1020 for removal during the implantation procedure. A proximal end of the cap member 1050 is seated in and engages a distal end of the implantable device 1060. Before the deployment instrument is inserted into the body, the implantable device 1060 is loaded into the deployment instrument at the distal end, and the cap member 1050 is attached to the device 1060 to close the exit opening 1020. During the implantation procedure, the cap member 1050 becomes removed from the exit opening 1020 as the implantable device 1060 is pushed forward through the deployment instrument. The cap member 1050 may be formed from a bioerodible or resorbable material, as described above, so that the cap member 1050 does not need to be removed from the body. Alternatively, the cap member 1050 may remain attached to the implantable device 1060 and may be removed with the implantable device following completion of treatment.

Figure 11:
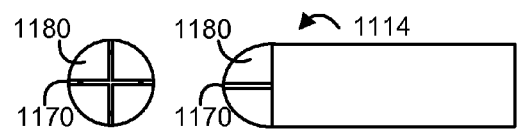
FIG. 11 is a plan view of a further embodiment of a distal end portion for a deployment instrument.

FIG. 11 is a side view of another embodiment of a deployment instrument distal tip portion 1114. As shown, the wall of the deployment instrument is rounded about the distal end. Slits 1170 are formed through the rounded portion to define a series of leaves 1180 in the wall about the distal end. The leaves 1180 are generally in a closed position, as shown in FIG. 11, but the slits 1170 permit the leaves 1180 to open. As the implantable device is pushed forward through the distal tip portion 1114 during the implantation procedure, the leaves 1180 open outward so that the implantable device can exit the deployment instrument. Once the implantable device has exited the deployment instrument, the leaves 1180 return to the closed position.

Figure 12:
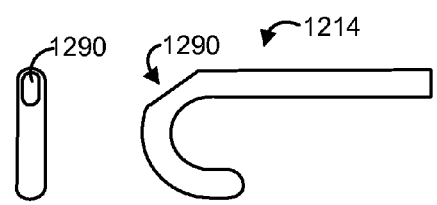
FIG. 12 is a plan view of yet another embodiment of a distal end portion for a deployment instrument.

FIG. 12 is a side view of an embodiment of a deployment instrument distal tip 1214 having a coude tip. The shape of the coude tip may be suited for navigating the male anatomy, particularly near the prostate. The coude tip may have an exit opening 1290 along a forward face, so that the device can exit the catheter.

Figure 13:
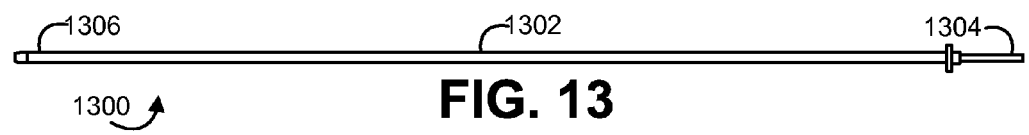
FIG. 13 is a plan view of an embodiment of a stylet.

In some embodiments, the deployment system further includes a stylet that can be used to drive the implantable device through at least a portion of the deployment instrument and into the implantation site. FIG. 13 is a plan view of an embodiment of a stylet 1300. Like the deployment instrument, the stylet 1300 includes a central body portion 1302, a proximal end portion 1304, and a distal end portion 1306. The central body portion 1302 is configured to extend through the interior passageway of the deployment instrument to reach the implantation site. The proximal end portion 1304 remains outside of the body and is configured for receiving a driving force from a user or apparatus. The distal end portion 1306 is configured for driving the device from the exit opening of the deployment instrument.

In some embodiments, the implantable device is loaded into the deployment instrument through the exit opening on its distal end portion. The implantable device travels through the urethra as the deployment instrument is inserted into the body, and subsequently, the stylet 1300 is used to drive the implantable device through the exit opening into the body. In other embodiments, the implantable device is loaded into the deployment instrument through the entry opening on its proximal end portion, either before or after the deployment instrument is inserted into the body, and subsequently the stylet 1300 is used to drive the implantable device through the deployment instrument and from the exit opening into the body. In still other embodiments, the implantable device is loaded into the deployment instrument through a slit along its central body portion. The implantable device travels partially the urethra as the deployment instrument is inserted into the body, and subsequently, the stylet 1300 is used to drive the implantable device through the remaining portion of the deployment instrument and from the exit opening into the body.

The overall shape and configuration of the stylet 1300 permits applying the driving force to the implantable device without substantial friction between the deployment instrument and the stylet 1300 and without the stylet 1300 causing trauma to the deployment instrument or the implantable device.

The dimensions of the stylet 1300 are selected based at least in part on the dimensions of the deployment instrument and the anatomy that the deployment instrument is designed to navigate. Particularly, the stylet 1300 may be slightly longer than the deployment instrument, so that the stylet 1300 can extend fully through the deployment instrument. Once inserted into the deployment instrument, the stylet proximal end portion 1304 is exposed outside of the proximal end portion of the deployment instrument, the stylet central body portion 1302 extends through the central body portion of the deployment instrument, and stylet distal end portion 1306 reaches to the distal end portion of the deployment instrument. Such a configuration permits inserting the stylet 1300 along the full length of the deployment instrument to drive the implantable device from the exit opening on the distal end of the deployment instrument. An outer diameter of the stylet 1300 is smaller than an inner diameter of the deployment instrument, so that the stylet 1300 can be inserted into the deployment instrument without having to overcome the force of friction along the length of the entire deployment instrument. In embodiments in which the deployment instrument has the dimensions described above, for extending through the urethra to the bladder, for example, the central body portion 1302 of the stylet 1300 may have a length in the range of about 35 cm to about 50 cm and an outer diameter in the range of about 2 mm to about 5 mm.

The stylet 1300 is formed from a material that has a column strength suited to reduce buckling, yet has a flexibility suited for navigating through the deployment instrument. The material is biocompatible and is compatible with the materials that are used to form the device and/or the catheter. The material is also amenable to sterilization procedures, such as gamma irradiation or ethylene oxide sterilization. Examples of suitable materials include both metals and polymers, such as stainless steel, cobalt-chromium-based alloys, titanium based alloys, Nitinol, polyethylene (PE), polytetrafluoroethylene (PTFE), styrenic thermoplastic elastomer (STE), silicone, latex rubber, polyurethane, Silitek®, C-flex®, Percuflex®, Tecoflex®, or combinations thereof. The stylet 1300 can be formed by extrusion, molding or other suitable manufacturing processes.

Figure 15:
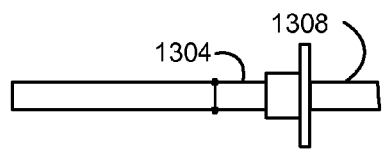
FIG. 15 is a cross-sectional plan view of a proximal end portion of the stylet shown in FIG. 13.

In the illustrated embodiment, the stylet 1300 has a substantially cylindrical outer surface, although other configurations are possible. The proximal end portion 1304 of the stylet 1300 is suited for interfacing with a user or equipment. In some embodiments, the proximal end portion 1304 is a handle 1308 that can be grasped by a user. The handle 1308 can be integrally formed with the stylet 1300, or the handle 1308 can be attached separately, such as by bonding. An example of a handle 1308 is shown in FIG. 15, although other configurations are possible.

Figure 14:
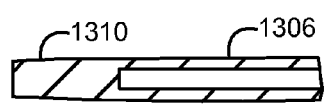
FIG. 14 is a cross-sectional plan view of a distal end portion of the stylet shown in FIG. 13.

For flexibility, the stylet 1300 may have a relatively hollow interior along at least a portion of its length, while the distal end portion 1306 may be substantially solid, or reinforced, to facilitate transferring the driving force to the device. An example is shown in FIG. 14, which illustrates the stylet 1300 having a hollow interior that terminates along the distal end portion 1306 so that the stylet 1300 has a substantially solid distal tip 1310.

The distal end portion 1306 of the stylet 1300 can have a range of configurations. In some embodiments, the distal end portion 1306 has an increased cross-sectional area in comparison to the central body portion 1302. Particularly, the central body portion 1302 has a reduced cross-sectional area to facilitate navigating turns through the deployment instrument with reduced friction, while the distal end portion 1306 has an increased cross-sectional area to facilitate transferring the driving force to the implantable device. The increased cross-sectional area increases the contact surface between the distal end portion 1306 and the implantable device. Further, the increased cross-sectional area of the distal end portion 1306 reduces the likelihood of the stylet 1300 traveling past the implantable device and potentially pinching or trapping the implantable device against the wall of the deployment instrument.

Figure 16:
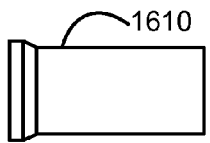
FIG. 16 is a plan view of an embodiment of a distal tip of a stylet.
Figure 17:
FIG. 17 is a plan view of another embodiment of a distal tip of a stylet.
Figure 18:
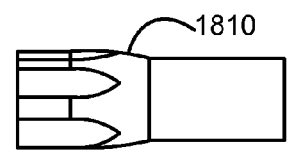
FIG. 18 is a plan view of an additional embodiment of a distal tip of a stylet.

Examples of distal end portions for the stylet 1300 shown in FIGS. 16-18. FIG. 16 is side view of a cupped-shaped distal tip portion 1610, which has a cupped-shaped surface at its distal end. The cupped-shaped surface has a larger cross-sectional area than the central body portion of the stylet. Thus, the cupped-shaped surface is suited for contacting the implantable device and transferring the driving force to the implantable device. In embodiments, the cupped-shaped surface has a cross-sectional area that is about the same as but is slightly smaller than the inner diameter of the deployment instrument, which reduces the likelihood of the stylet traveling past the implantable device without engaging the implantable device, and yet does not create unsuitable friction between the cupped-shaped surface and the wall of the deployment instrument. Although the surface is shown and described as being cupped-shaped, the surface can be convex, concave, or flat depending on the embodiment. For example, FIG. 17 is side view of an angled distal tip portion 1710. The angled distal tip portion 1710 has a increased cross-sectional area in comparison to the stylet central body portion, but unlike the cupped-shaped distal tip portion 1610, the distal surface of the angled distal tip portion 1710 is flat and angled.

FIG. 18 is side view of a fluted distal tip portion 1810. The fluted distal tip portion 1810 is similar to the cupped-shaped distal tip portion 1610, in that the fluted distal tip portion 1810 has an increased cross-sectional area at a distal end for contacting the implantable device and driving the device forward. The fluted-distal tip portion 1810 also has a fluted exterior, which permits fluid to drain past.

In some embodiments, the deployment instrument is designed to receive a stream of fluid that drives the implantable device into the implantation site. In such embodiments, the deployment instrument may connect to a fluid source, such as syringe, so that the stream of fluid can be driven into the deployment instrument. The deployment instrument may have a luer connector that facilitates operably associating the deployment instrument with the fluid source, although other configurations are possible.

Figure 19:
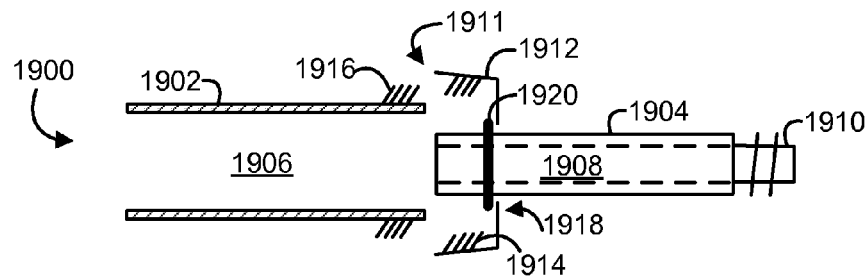
FIG. 19 is a cross-sectional plan view of an embodiment of a stylet associated with a deployment instrument.

FIG. 19 is a cross-sectional plan view of an embodiment of a deployment system 1900 that includes a deployment catheter 1902 and a stylet 1904. The deployment catheter 1902 and stylet 1904 are movable with reference to each other, so that the stylet 1904 can be used to push the implantable device toward the bladder. The deployment catheter 1902 and stylet 1904 also form a continuous fluid path for delivering fluid to and from the bladder, such as for distending or draining the bladder, yet the deployment catheter 1902 and stylet 1904 can be sealed with reference to each other to reduce leakage.

In particular, the stylet 1904 has a reduced cross-section with reference to the deployment catheter 1902 so that the stylet 1904 can fit inside an internal lumen 1906 of the deployment catheter 1902. The stylet 1904 also includes an internal lumen or channel 1908, and when the stylet 1904 is inserted into the deployment catheter 1902, the internal lumen 1908 of the stylet 1904 is in fluid communication with the internal lumen 1906 of the deployment instrument 1902. A fluid port 1910, such as a luer connector, slip tip, or other suitable fluid source connection means, may be formed on a proximal end of the stylet 1904 for introducing fluid to, or receiving fluid from, the stylet internal lumen 1908. A seal 1911 is formed between the deployment catheter 1902 and stylet 1904, reducing leakage. In the illustrated embodiment, for example, the seal includes a threaded cap 1912 positioned on the distal end of the stylet 1904. The threaded cap 1912 includes internal threads 1914 that are configured to engage external threads 1916 about the proximal end of the deployment catheter 1902. The threaded cap 1912 has an opening 1918 that permits the stylet 1904 to pass through the threaded cap 1912 into the deployment catheter 1902. An O-ring 1920 is positioned adjacent to the opening 1918 to reduce leakage.

Figure 20:
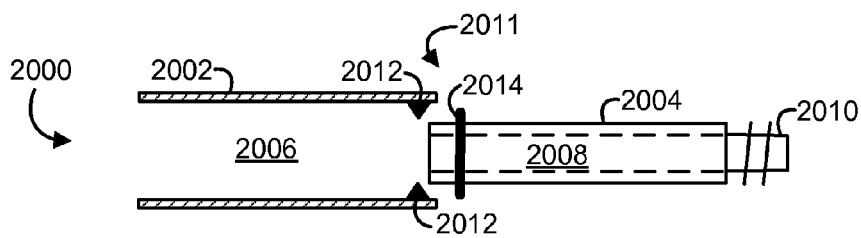
FIG. 20 is a cross-sectional plan view of another embodiment of a stylet associated with a deployment instrument.

FIG. 20 is a cross-sectional plan view of another embodiment of a deployment system 2000 that includes a deployment catheter 2002 and a stylet 2004. Like the deployment system 1900, the deployment catheter 2002 and stylet 2004 can move with reference to each other, form a continuous fluid path for delivering fluid to and from the bladder, and can be sealed with reference to each other to reduce leakage. The stylet 2004 has a reduced cross-section with reference to the deployment catheter 2002 so that the stylet 2004 can fit inside an internal lumen 2006 of the deployment catheter 2002. The stylet 2004 also includes an internal lumen 2008 that is in fluid communication with the internal lumen 2006 of the deployment instrument 2002 when the stylet 2004 is inserted into the deployment catheter 2002. The stylet 2004 also includes the fluid port 2010, such as a luer connector, slip tip, or other suitable fluid source connection means, for introducing fluid to or receiving fluid from, the stylet internal lumen 2008, and a seal 2011 is formed between the deployment catheter 2002 and stylet 2004 to reduce leakage. In FIG. 20, the seal 2011 includes a protruding rim 2012 or shoulder concentrically positioned about the interior of the deployment catheter 2002 and an O-ring or seal 2014 concentrically positioned about the exterior of the stylet 2004. The rim 2012 and O-ring 2014 are sized to engage each other as the stylet 2004 is driven through the deployment catheter 2002, forming a seal 2011 that reduces leakage.

Figure 21:
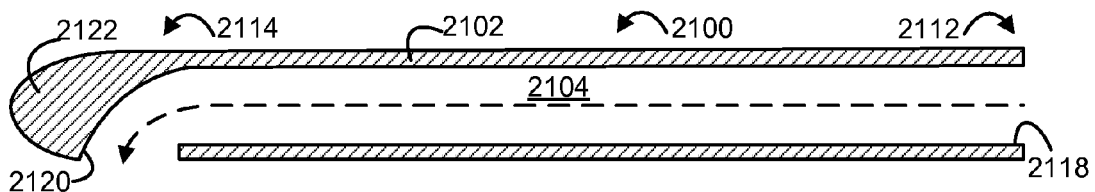
FIG. 21 is a cross-sectional plan view of another embodiment of a deployment instrument.

FIG. 21 is a cross-sectional plan view of such an embodiment of a deployment instrument 2100. The deployment instrument 2100 generally includes a catheter having an internal lumen 2104, a fluid introduction port 2118 located at its proximal end, and an exit opening 2120 locating at a distal end. Both the fluid introduction port 2118 and the exit opening 2120 are in fluid communication with the internal lumen 2104. In the illustrated embodiment, the deployment instrument 2100 has a reinforced distal end 2122, much like the deployment instrument shown in FIG. 6. The distal opening 2120 is positioned on the distal end of the deployment instrument 2100 offset from its longitudinal axis. The offset placement of the distal opening 2120 permits configuring the distal tip 2122 for advancing through the urethra without causing trauma. For example, the distal tip 2122 may include a rounded portion, which may be solid and/or reinforced. The distal opening 2120 may be positioned on the rounded portion offset from center or the distal opening 2120 may be formed along a side of the deployment instrument through the wall 2102 near the rounded portion. Other configurations are possible.

In use, the deployment instrument 2100 is inserted through the urethra. The implantable device may be pre-loaded into the deployment instrument 2100, positioned near the distal end portion 2114, so that introducing the deployment instrument 2100 into the body simultaneously introduces the implantable device into the body. However, other configurations are possible. For example, the implantable device may be loaded into the deployment instrument 2100 after the deployment instrument 2100 is introduced into the body, and the implantable device may be advanced along the length of the deployment instrument 2100 to the distal end, using a stream of fluid, a push rod or stylet, or a combination thereof.

Once the distal end portion 2114 of the deployment instrument 2100 is positioned in the bladder, urine may enter the distal opening 2120 and may travel along the length of the internal lumen 2104 to the fluid introduction port 2118. The return of urine through the fluid introduction port 2118 indicates proper placement of the deployment instrument 2100 in the body with the distal end portion 2114 located in the bladder.

A volume of water or other suitable fluid then may be introduced into the bladder to form a cushion for the implantable device. For example, a syringe of water may be operably associated with the fluid introduction port 2118. The syringe may block the fluid introduction port 2118 to prevent the further escape of urine. The syringe 2118 may be depressed to introduce water into the bladder, inflating the bladder to provide a cushion for the implantable device. About 50 to 60 mL of water may be introduced into the bladder, although other volumes of water may be used. In cases in which the implantable device is positioned in the internal lumen 2104, the water may travel about spaces between the implantable device and the wall of the deployment instrument 2100. The force of the water traveling through the internal lumen 2104 may or may not advance the implantable device forward.

Once the bladder has been inflated, the proximal end portion 2112 of the deployment instrument may be blocked adjacent to the fluid introduction port 2118 to prevent the return of water or urine as the syringe of water is removed. For example, an external clamp may be applied to the deployment catheter. One suitable clamp is an Easy Reopening Closure Clamp made by the Qosina Corporation of Edgewood, N.Y. The clamp may not cause permanent deformation to the deployment instrument 2102 due to the compliant nature of its walls 2102.

A syringe of fluid is then placed in fluid communication with the fluid introduction port 2118. The clamp is removed and the syringe is pushed to eject the fluid. The fluid is communicated through the fluid introduction port 2118 and along the length of the deployment instrument 2100 to drive the implantable device from the distal end of the deployment instrument 2100 into the bladder. Thereby, the implantable device is implanted. Thereafter, a push-rod or stylet may be inserted through the deployment instrument 2100 to verify that the implantable device has exited the deployment instrument 2100 into the bladder.

The amount of fluid needed to implant the implantable device may vary depending on the dimensions of the deployment instrument 2100. For example, about 10 to 20 mL of fluid may be injected. Suitable fluids are relatively viscous, water-soluble, biocompatible, incompressible, and do not negatively interact with the deployment instrument 2100 or the implantable device. Suitable fluids also may not interfere with any drug delivered from the implantable device once implanted. In one example, the fluid may comprise a lubricant, such as Surgilube brand lubricant, which is manufactured by Fougera Inc. of Melville, N.Y. Other suitably viscous fluids also may be used. For example, the fluid may have a viscosity that exceeds the viscosity of water. Injecting a suitably viscous fluid into the deployment instrument 2100 may drive the implantable device forward despite the weight of the implantable device and the force of friction, such as friction between the implantable device and the wall 2102 of the deployment instrument 2100. However, less viscous fluids such as water may be used. Although the deployment instrument is described as receiving a stream of fluid from a syringe, other fluid sources can be used.

The method of implanting a drug delivery device described above with reference to FIG. 21 is merely one example, and other implantation methods are possible. For example, it may not be necessary to introduce water into the bladder before the implantable device is implanted. It also may not be necessary to verify implantation of the drug delivery device with a push-rod or stylet. Further, the deployment instrument 2100 may have other configurations. For example, the deployment catheter 2100 may have more than one port on its proximal end. Also, the port may be associated with a valve that can be moved from an open position to a closed position to prevent fluid from exiting the port. In such embodiments, it may not be necessary to clamp the deployment instrument during the implantation procedure. The deployment instrument also may have a luer connector or a slip tip on one or more of the ports to facilitate operably associating the deployment instrument with a fluid source. In some embodiments, the deployment instrument is divided into a number of discrete lumens, such as two or three lumens. Each discrete lumen may be associated with one or more ports. Further, each port may be operably associated with valve. A range of combinations of lumens, ports, and valves can be used to achieve a suitable deployment instrument.

Figure 22:
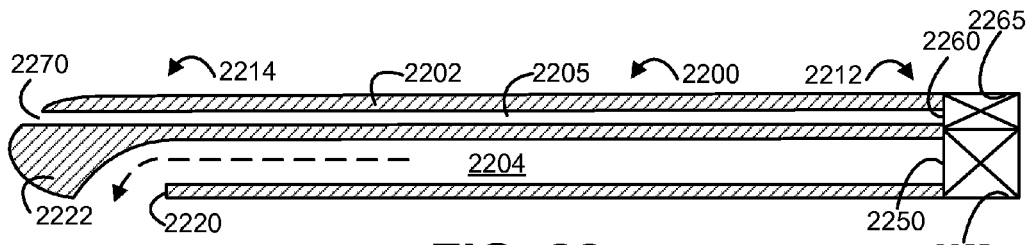
FIG. 22 is a cross-sectional plan view of an additional embodiment of a deployment instrument.

For example, FIG. 22 illustrates a deployment instrument 2200 having a main lumen 2204 in communication with a main port 2250 and a urine return lumen 2205 in communication with a urine return port 2260. Each port 2250, 2260 may be associated with a valve 2255, 2265 that can be opened or closed to permit or prevent the flow of fluid there through. For example, the valve 2255 on the main port 2250 can be opened to permit the introduction of fluid into the main lumen 2204 for the purpose of driving the implantable device forward, and the valve 2255 can be closed to prevent fluid from returning through the main port 2250. The valve 2265 on the urine return port 2260 may be opened to permit the return of urine through the urine return lumen 2205 and can be closed to prevent the continued return of urine once placement of the deployment instrument 2200 in the bladder has been verified.

In use, the deployment instrument 2200 may be inserted through the urethra with the valve 2255 on the main port 2250 closed and the valve 2265 on the urine return port 2260 open. Thus, when the distal end portion 2214 of the deployment instrument 2200 becomes positioned in the bladder, urine can enter the urine return opening 2270 on the distal top of the deployment instrument 2200. The urine travels through the urine return lumen 2205 and from the urine return port 2260 to indicate placement of the distal tip of the deployment instrument 2200 in the bladder. Once placement is confirmed, the valve 2265 associated with the urine return port 2260 may be closed to prevent the continued return of urine. A syringe or other fluid introduction mechanism is then operably associated with the main port 2250. The valve 2255 on the main port 2250 is opened, and fluid is introduced from the syringe through the main port 2250 to drive the implantable device into the bladder. The main port 2250 is then closed. In some embodiments, delivery of the implantable device from the deployment instrument 2200 may be verified using a push-rod or stylet. The push rod is inserted into the main port 2250, the valve 2255 is opened, and the push rod is inserted along the length of the deployment instrument 2200 to verify delivery of the implantable device from the deployment instrument 2200. It should be noted that the valves 2255, 2265 may be substituted with external clamps in these and in other embodiments. The external clamp may be removably positioned about the ports 2250, 2260 to permit or prevent the flow of fluid as needed. In these and in other embodiments, the ports 2250, 2260 may be angled or spaced apart from each other, as shown in FIG. 23.

Figure 23:
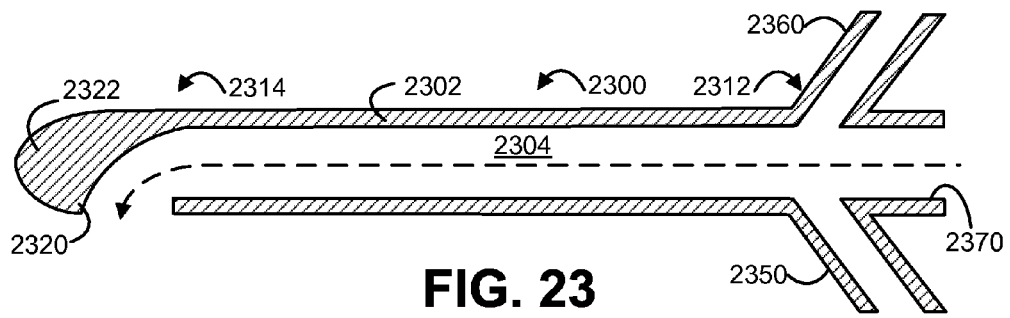
FIG. 23 is a cross-sectional plan view of a further embodiment of a deployment instrument.

FIG. 23 illustrates a deployment instrument 2300 having a central lumen 2304 operably associated with a fluid introduction port 2350, a urine return port 2360, and a push-rod port 2370. The use of the deployment instrument 2300 is similar to the use of the deployment instrument 2200 shown in FIG. 22. Each port may be associated with a valve that can be opened or closed to permit or prevent the flow of fluid through the ports. For example, the valve on the fluid introduction port 2350 can be opened to permit the introduction of fluid into the central lumen 2304 for the purpose of driving the implantable device forward and can be closed to prevent the introduced fluid from returning through the fluid introduction port 2350. The valve on the urine return port 2360 also may be opened to permit the return of urine, indicating placement of the deployment instrument 2300 in the bladder, and can be closed to prevent the continued return of urine once placement has been verified. The valve on the push-rod port 2370 may be opened to introduce a push-rod into the central lumen 2304 for the purpose of verifying the implantable device has exited the deployment instrument 2300 or for driving the implantable device from the deployment instrument 2300, and may be closed thereafter.

In use, the urine return port 2360 may be opened and the fluid introduction and push-rod ports 2350, 2370 may be closed as the deployment instrument 2300 is deployed through the urethra, so that urine can return through the central lumen 2304 and from the urine return port 2360 to indicate placement of the distal tip portion 2314 in the bladder. Once placement is confirmed, the valve associated with the urine return port 2360 may be closed. A syringe or other fluid introduction mechanism is associated with the fluid introduction port 2350. The valve on the fluid introduction port 2350 is opened, and fluid is introduced from the syringe through the fluid introduction port 2350 to drive the implantable device into the bladder. The fluid introduction port 2350 is then closed, and a push rod is inserted into the push-rod port 2370. The valve on the push-rod port 2370 is opened, and the push rod is inserted along the length of the deployment instrument 2300 to verify delivery of the implantable device from the deployment instrument 2300. However, verification with the push rod is not necessary, in which case the push-rod port 2370 may be omitted. It should be noted that the valves may be substituted with external clamps in these and in other embodiments. The external clamp may be removably positioned about the deployment instrument 2300 to permit or prevent the flow of fluid as needed. Additionally, some or all of the ports may share a single valve positioned upstream from the ports on the deployment instrument 2300.

Figure 24:
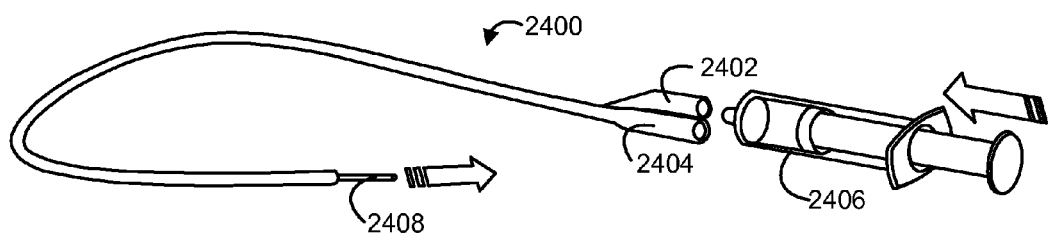
FIG. 24 is a perspective view of an embodiment of a deployment instrument.
Figure 25:
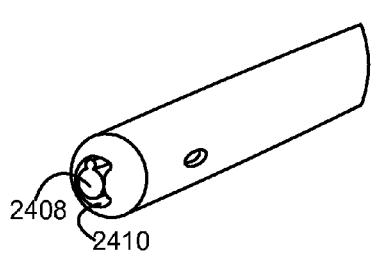
FIG. 25 is a perspective view of a distal end portion of the deployment instrument shown in FIG. 24.
Figure 26:
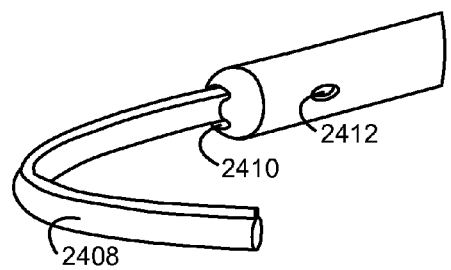
FIG. 26 is another perspective view of the distal end portion of the deployment instrument shown in FIG. 24, illustrating an implantable device exiting the deployment instrument.

FIG. 24 illustrates another embodiment of a deployment instrument 2400 for delivering an implantable device to the bladder. The deployment instrument 2400 generally includes a catheter having a fluid introduction port 2402 located at its proximal end, and a syringe of fluid 2406 in fluid communication with the fluid introduction port 2402. In use, the implantable device 2408 is pre-loaded into an exit opening 2410 on the distal end of the deployment instrument 2400, as shown in FIG. 25. The exit opening 2410 also may be formed through a side of the deployment instrument 2400 so that the distal end can be reinforced, as described above. The deployment instrument 2400 is then introduced into the body. When the syringe 2406 is pushed to eject the fluid, the fluid is communicated through the fluid introduction port 2402 and along the length of the deployment instrument to drive the implantable device 2408 from the exit opening 2410 in the distal end of the deployment instrument into the bladder, as shown in FIGS. 24 and 26. Thereby, the implantable device 2408 is implanted.

In some embodiments, the deployment instrument 2400 is divided into two discrete lumens. A central lumen is sized for receiving the implantable device 2408, which is loaded into the central lumen. In some embodiments, the cross-sectional shape of the central lumen may match the cross-sectional shape of the implantable device. The central lumen is also in fluid communication with the fluid introduction port 2402. Thus, fluid introduced through the fluid introduction port 2402 travels through the central lumen to drive the implantable device 2408 into the bladder.

A secondary lumen is also provided. The secondary lumen extends from a secondary opening 2412 at a distal end of the deployment instrument 2400 to a fluid exit port 2404 positioned at the proximal end of the deployment instrument 2400, such as adjacent to the fluid introduction port 2402. The secondary lumen can transport fluid from the distal end of the deployment instrument 2400 to the proximal end and out of the fluid exit port 2404. In use, when the distal end of the deployment instrument 2400 enters the bladder, urine from the bladder enters the secondary opening 2412 at the distal end and travels through the secondary lumen to the fluid exit port 2404 on the proximal end. The return of urine through the secondary lumen indicates the distal end has become positioned in the bladder. In such embodiments, the secondary opening 2412 can be thought of as a urine entry opening, the secondary lumen can be thought of as a urine return lumen, and the fluid exit port 2404 can be thought of as a urine exit port.

In some embodiments, the urine entry opening 2412 can be formed through a distal end surface of the deployment instrument 2400, so that urine can enter the urine return lumen as soon as the distal end surface of the deployment instrument 2400 has entered the bladder. In other embodiments, the urine entry opening 2412 can be formed through a side of the deployment instrument 2400, rearward of the distal surface by a predetermined distance, so that urine can enter the urine return lumen as soon as the distal end of the deployment instrument 2400 has passed the predetermined distance into the bladder. Such an embodiment in shown in FIG. 26. In some embodiments, the urine return lumen is sized to impede urine flow, so that the urine exit port 2404 can be left unattended. In such embodiments, a vacuum can be applied to the urine exit port 2404 to cause urine to travel through the urine return lumen, so that the user can determine whether the distal end of the deployment instrument 2400 is properly positioned in the bladder. In other embodiments, the urine exit port 2404 may be associated with a plug, or a stop, that is operable to block the return of urine once initial placement of the deployment instrument 2400 has been verified. However, the urine return lumen is not necessary and may be omitted.

In some embodiments, the deployment system 2400 is used in conjunction with a stylet. The lubricant or other suitable fluid is introduced through the fluid introduction port 2402 before the stylet is inserted. Thus, when the stylet is driven along the length of the deployment instrument 2400, the stylet forces the fluid forward, which carries the implantable device 2408 forward and out of the exit opening 2410. In such embodiments, the stylet may have an outer diameter that is slightly smaller than an inner diameter of the central lumen, and the fluid may be relatively incompressible and viscous, so that the fluid does not leak about the stylet or the implantable device 2408 but instead is pushed forward along with the device 2408.

In such embodiments, the implantable device 2408 and the fluid can be positioned in the deployment instrument 2400 before the deployment instrument 2400 is inserted into the body. Once the deployment instrument 2400 is positioned in the body, the stylet is inserted along the length of the deployment instrument 2400 to drive the fluid and the implantable device 2408 forward until the device 2408 exits the exit opening 2410 into the bladder. Alternatively, one or both of the implantable device 2408 and the fluid can be inserted into the deployment instrument 2400 after the deployment instrument 2400 is positioned in the body. The fluid may also be omitted, in which case the stylet directly contacts the implantable device 2408 to drive the device into the bladder.

Figure 27:
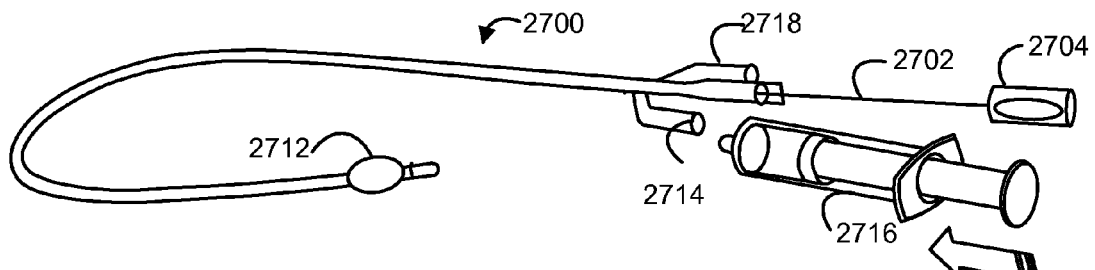
FIG. 27 is a perspective view of another embodiment of a deployment instrument.

FIG. 27 illustrated another embodiment of a deployment instrument 2700 for delivering an implantable device into the bladder. The deployment instrument 2700 generally includes a plunger 2702 and a handle 2704 operatively connected to the plunger 2702. The handle 2704 is positioned at the proximal end of the deployment instrument 2700. The plunger 2702 extends from the handle 2704 through a central lumen of the deployment instrument 2700. The plunger 2702 is positioned rearward of the distal end of the deployment instrument 2700. In use, the implantable device 2706 is pre-loaded into the distal end of the deployment instrument 2700, and the deployment instrument 2700 is introduced into the body. When the handle 2704 is pushed, the plunger 2702 travels forward along the length of the deployment instrument 2700 to drive the implantable device 2706 from the distal end of the deployment instrument 2700 into the bladder. Thereby, the implantable device 2706 is deployed or implanted.

Figure 28:
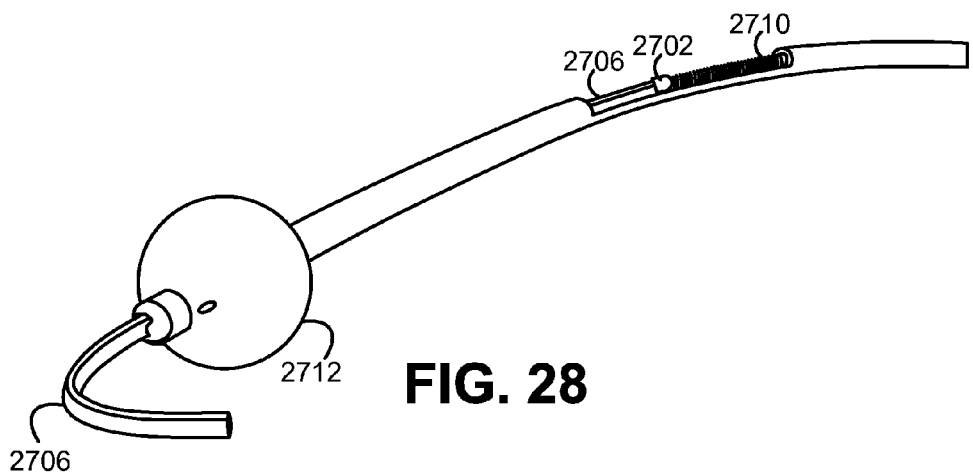
FIG. 28 is a perspective view of a distal end portion of the deployment instrument shown in FIG. 27, illustrating an implantable device exiting the deployment instrument.

In certain embodiments, the plunger 2702 is associated with a spring 2710 that is configured to magnify the driving force of the user on the handle 2704. The plunger 2702 and spring 2710 are visible in FIG. 28, which illustrates a perspective partial cut-away view of the distal end portion of the deployment instrument 2700. In some embodiments, the spring 2710 reverses the direction of the driving force. In such embodiments, the implantable device 2706 is driven forward by pulling the handle 2704 rearward.

In some embodiments, the deployment instrument 2700 is a Foley catheter suited for retaining the deployment instrument in the bladder. The deployment instrument 2700 has a balloon 2712 located about its distal end. The balloon 2712 is in fluid communication with a fluid entry port 2714 on the proximal end of the deployment instrument 2700 by way of a secondary lumen through the deployment instrument 2700. In use, fluid introduced through the fluid entry port 2714, such as via a syringe 2716, travels along the secondary lumen to inflate the balloon 2712. Thus, the fluid entry port 2714 can be thought of as a Foley balloon inflation port, and the secondary lumen can be thought of as a Foley balloon inflation lumen. Once the balloon is inflated, the balloon 2712 may impede the deployment instrument 2700 from traveling rearward through the urethra, such that the distal end of the deployment instrument 2700 is retained in the bladder. However, the Foley balloon 2712 and corresponding port 2714 and lumen can be omitted. In the illustrated embodiment, the deployment instrument 2700 further includes a urine return port 2718 in communication with a urine return opening on the distal end of the deployment instrument 2700 via a urine return lumen. The urine return port 2718 facilitates determining when the distal end has become positioned in the bladder so that the Foley balloon 2714 is not inflated prematurely. Thus, the illustrated deployment instrument 2700 has three internal lumens, each of which is in communication with separate openings on distal and proximal ends of the deployment instrument 2700. However, one or both of the Foley balloon inflation lumen and/or the urine return lumen may be omitted, along with its corresponding ports and openings.

As described above, the implantable device may be implanted by injecting a fluid into a deployment instrument. The fluid may drive the implantable device along the deployment instrument into the bladder. In some embodiments, a movable seal or transfer plug may be positioned between the fluid and implantable device. The movable seal or transfer plug may transfer the driving force of the fluid to the implantable device. In particular, the movable seal or transfer plug may be configured to increase the portion of the available driving force that is transferred directly to the implantable device, such as by reducing the amount of driving fluid that travels past the implantable device without acting on the device to drive it forward. In addition, the movable seal or transfer plug may facilitate using a less viscous driving fluid, such as water. Embodiments of a movable seal or transfer plug are described below with reference to FIGS. 29 through 31.

Figure 29:
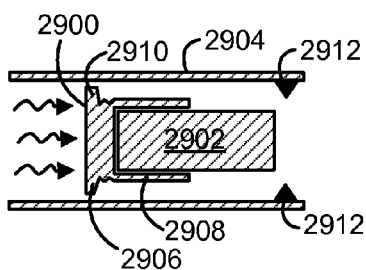
FIG. 29 is a cross-sectional plan view of an embodiment of a transfer plug associated with an implantable device.

FIG. 29 is a cross-sectional view of an embodiment of a plunger 2900 that can be positioned about an end of an implantable device 2902 to facilitate driving the implantable device 2902 through the deployment instrument 2904. In particular, the implantable device 2902 may have a smaller cross-section than the deployment instrument 2904. When lubricant is used to drive the implantable device 2902 through the deployment instrument 2904, the lubricant may escape about the implantable device 2902 instead of driving the implantable device 2902 forward. Thus, the plunger 2900 can be used to increase the cross-sectional area of the implantable device 2902 about at least a proximal end so that the lubricant is impeded from passing between the implantable device 2902 and the deployment instrument 2904.

The plunger 2900 is generally formed from a flexible material, such as rubber. The plunger 2900 may be cap-shaped, having a head portion 2906 and a flange portion 2908. The head portion 2906 may have an outer rim 2910 that corresponds in shape and size to the internal lumen of the deployment instrument 2904. The outer rim 2910 contacts the wall of the deployment instrument 2904, forming a seal with the deployment instrument 2904.

The flange portion 2908 defines an opening or cavity that can matingly engage at least a portion of the implantable device 2902. The flange portion 2908 may have an outer cross-section that is smaller than the internal lumen of the deployment instrument 2904 to reduce contact between the plunger 2902 and the wall of the deployment instrument 2904, thereby reducing friction. Also, the flange portion 2908 may not be continuous about its entire circumference to reduce the weight of the plunger 2902 and to further reduce the likelihood of contact with the wall of the deployment instrument 2904.

The deployment instrument 2904 may have at least one stop 2912 configured to impede forward movement of the plunger 2900 past a certain point. The stop 2912 may be a rim or a series of nubs that project from the wall of the deployment instrument 2904 into its lumen.

In use, the plunger 2900 is operably associated with the implantable device 2902 such that the proximal end of the implantable device 2902 becomes seated in the opening in the flange portion 2908. The plunger 2900 and implantable device 2902 are then loaded into the deployment instrument 2904. The outer rim 2910 forms a seal with the wall of the deployment instrument 2904, and fluid is introduced into the deployment instrument 2904. The force of the fluid against the head portion 2906 drives the plunger 2900, and therefore the implantable device 2902, forward. Once the implantable device 2902 has been delivered from the deployment instrument 2904, the outer rim 2910 of the plunger 2900 may contact the stop 2912 to prevent the plunger 2900 from continued forward travel. Thus, the implantable device 2902 may be implanted but the plunger 2900 may remain in the deployment instrument 2904.

The plunger 2900 impedes the driving fluid from passing between the implantable device 2900 and the wall of the deployment instrument 2904 instead of driving the implantable device 2902 forward. Thus, the implantable device 2902 may be implanted using a lower viscosity fluid, such as water. The driving fluid may not contact the implantable device 2902 during the implantation process due to the presence of the plunger 2900.

Figure 30:
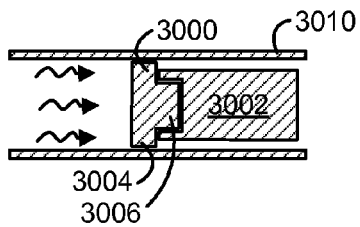
FIG. 30 is a cross-sectional plan view of another embodiment of a transfer plug associated with an implantable device.

FIG. 30 is a cross-sectional view of another embodiment of a plunger 3000 positioned about an end of an implantable device 3002. As shown, the plunger 3000 is generally a cap piece that is attached to the proximal end of the implantable device 3002. The cap has a head portion 3004 and a tip portion 3006. The head portion 3004 corresponds in shape and size to the internal lumen of the deployment instrument 3010, while the tip portion 3006 corresponds in size and shape to an internal lumen in the implantable device 3002. In use, the plunger 3000 is attached to the implantable device 3002 by inserting the tip portion 3006 into the implantable device 3002, and the implantable device 3002 is loaded into the deployment instrument 3010. The head portion 3004 of the plunger 3000 contacts the wall of the deployment instrument 3010, forming a seal, and fluid is introduced into the deployment instrument 3010 to drive the implantable device 3002 forward. The plunger 3000 is implanted with the implantable device 3002 and is either removed or resorbed with the device 3002.

Figure 31:
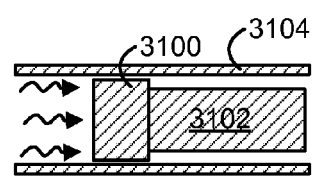
FIG. 31 is a cross-sectional plan view of an embodiment of a transfer plug positioned adjacent to an implantable device.

FIG. 31 is side view of another embodiment of a transfer plug or movable seal 3100 that is separate from the implantable device 3100. The transfer plug 3100 has a cross-sectional area that is about the same as the deployment instrument

3104, while the implantable device 3102 has a cross-sectional area that is smaller than the deployment instrument 3104. The transfer plug 3100 may facilitate transferring the driving force of the fluid to the implantable device 3102. The transfer plug 3100 may be attached to the implantable device 3102, or the transfer plug 3100 may be separate from the implantable device 3102, in which case the transfer plug 3100 may be formed from a resorbable material, so that the transfer plug 3100 can be driven into the bladder along with the implantable device 3102 and subsequently is resorbed.

It should be noted that any of the embodiments of plungers, movable seals, or transfer plugs shown and described in FIGS. 29-31 can be used in association with a stylet instead of a flow of fluid. In such cases, the plunger, movable seal, or plug may be attached to the stylet instead of the implantable device, or the plunger, movable seal, or plug may be separate from both the stylet and the implantable device, in which case a resorbable material may be used, although other configurations are possible.

The deployment instrument may be provided as a kit. In some embodiments, the deployment instrument further includes at least one package that houses one or more of the instrument, a stylet, a syringe, and the implantable device. The package protects the packaged components before the implantation procedure. For example, the components may be sterilized together, and transported together, in the package. In such embodiments, the implantable device can be pre-loaded into the deployment instrument before the deployment instrument is placed in the package, which eliminates the need to load the implantable device during the implantation procedure, reducing the number of steps in the procedure and reducing the risk that the implantable device will be dropped inadvertently or damaged during loading. However, the implantable device need not be pre-loaded. Instead, the implantable device can be provided along side the deployment instrument or can be packaged separately. Also, the stylet can be either be packaged with the deployment instrument, packaged separately, or omitted completely. Regardless of which components are packaged together, the package is sterilized, such as using gamma irradiation or ethylene oxide sterilization.

Figure 32:
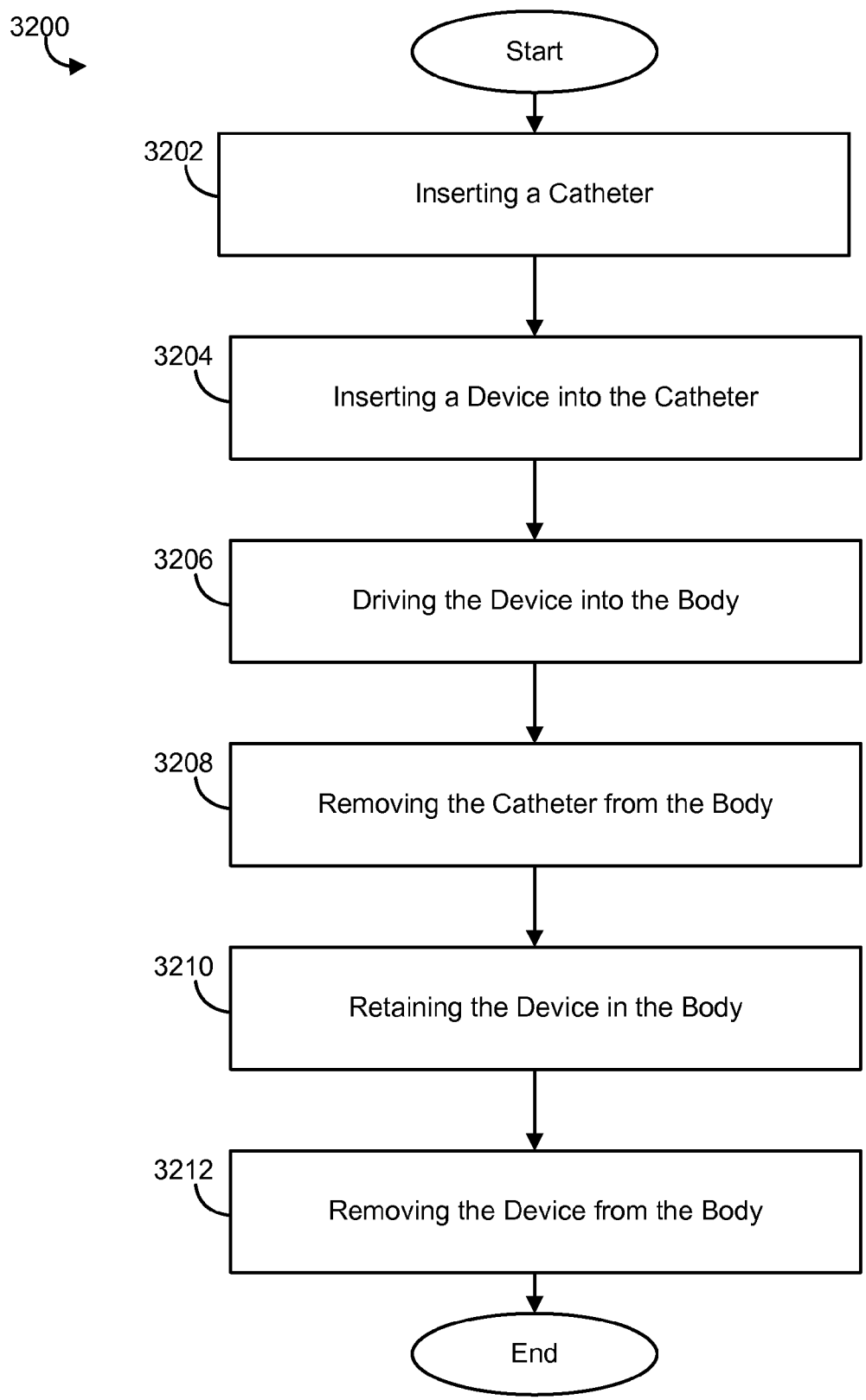
FIG. 32 is a block diagram of an embodiment of a method of implanting an implantable device in the bladder.

FIG. 32 is a block diagram illustrating an embodiment of a method 3200 for implanting an implantable device into the bladder, such as an implantable drug delivery device. In block 3202, a deployment instrument is inserted into the body. The deployment instrument may be an embodiment of the deployment instrument described above, although other deployment instrument may be used. For example, the deployment instrument may be a catheter or a cystoscope, either conventionally known or specially developed for this purpose. Inserting the deployment instrument generally includes inserting the deployment instrument into the urethra and driving the deployment instrument forward until a distal end is positioned in the bladder, while a proximal end remains outside of the body.

In some embodiments, the deployment instrument is inserted into the body in block 3202 in association with a cystoscope, which permits visualizing the implantation procedure. The cystoscope may be rigid or flexible and may include an interior channel. A rigid cystoscope may be preferred for female patient, while a flexible cystoscope may be preferred for male patients. In use, the cystoscope is inserted through the urethra and the deployment instrument is inserted through the interior channel of the cystoscope until the distal end of the deployment instrument reaches the bladder. In such embodiments, the deployment instrument may not need to have a mechanical stiffness or column strength suited for insertion through the urethra directly.

In some embodiments, inserting the deployment instrument into the body in block 3202 further includes verifying a distal end of the deployment instrument has become positioned in the bladder. For example, the location of the distal end can be verified by communicating urine through the deployment instrument from the distal end positioned in the bladder. The location of the distal end also can be verified by visualizing the distal end of the deployment instrument with a cystoscope, an ultrasound or x-ray. Also in some embodiments, inserting the deployment instrument into the body in block 3202 further includes securing a distal end of the deployment instrument in the bladder, such as by inflating a balloon positioned on the distal end.

In block 3204, the implantable device is inserted into the deployment instrument. The implantable device can be any suitable device, including embodiments of the device 100 described above. In some cases, inserting the implantable device into the deployment instrument can include deforming the implantable device from a retention shape to a deployment shape. Inserting the implantable device into the deployment instrument may include inserting the implantable device into the deployment instrument distal end, into the deployment instrument proximal end, or into an opening or slit along the deployment instrument central body portion. In some cases, inserting the implantable device into the deployment instrument comprises pre-loading the implantable device into the deployment instrument before the deployment instrument is inserted into the body. In such cases, the order of blocks 3202 and 3204 is reversed. The implantable device is typically pre-loaded if the device is placed in the deployment instrument through the distal end or central body portion, although the implantable device can be pre-loaded in any case for convenience. The implantable device may be lubricated before the implantable device is inserted into the deployment instrument, to reduce friction associated with driving the implantable device through the deployment instrument in block 3206.

In block 3206, the implantable device is driven into the bladder. In embodiments in which the implantable device is inserted into the deployment instrument proximal end portion in block 3204, driving the implantable device into the bladder includes driving the implantable device from the deployment instrument proximal end portion, along the deployment instrument central body portion, and through the deployment instrument distal end portion until the implantable device exits the deployment instrument into the bladder. In embodiments in which the implantable device is inserted into the deployment instrument distal end in block 3204, driving the implantable device into the bladder includes driving the implantable device through the deployment instrument distal end portion until the implantable device exits the deployment instrument into the bladder, as the implantable device was previously driven through the urethra upon insertion of the deployment instrument in block 3202.

In some embodiments, driving the implantable device into the bladder in block 3206 comprises driving the implantable device with a stylet. The stylet may be an embodiment of the stylet described above. In such cases, driving the implantable device into the bladder in block 3206 includes inserting the stylet distal end portion into the deployment instrument proximal end portion and advancing the stylet through the deployment instrument until the stylet distal end portion reaches the deployment instrument distal end portion. In embodiments in which the implantable device is loaded into the deployment instrument proximal end portion, driving the implantable device into the bladder in block 3206 includes contacting the implantable device with the stylet, advancing the implantable device through the deployment instrument using the stylet, and driving the implantable device from the deployment instrument with the stylet. In embodiments in which the implantable device is preloaded into the deployment instrument distal end portion, driving the implantable device into the bladder in block 3206 includes advancing the stylet through the deployment instrument to the implantable device located at the deployment instrument distal end portion, contacting the implantable device with the stylet, and driving the implantable device from the deployment instrument with the stylet.

In other embodiments, driving the implantable device into the bladder in block 3206 comprises driving a stream of fluid into the deployment instrument. The stream of fluid may be a stream of incompressible lubricant, as described above. In such embodiments, driving the implantable device into the bladder may further comprise associating the proximal end of the deployment instrument with a fluid source such that a fluid-tight seal is formed. For example, a luer connector on the deployment instrument proximal end may be attached to a source of lubricant. The lubricant may be driven from the source of lubricant through the deployment instrument, pushing the implantable device forward until the device exits into the bladder. Thereafter, the lubricant may be naturally flushed from the body.

In embodiments in which the method implants a device that is configurable between a deployment shape and a retention shape, driving the implantable device from the deployment instrument in block 3206 removes the force of the deployment instrument wall from the implantable device, which may cause the implantable device to naturally return to the retention shape for retention in the bladder. An example is shown in FIG. 4 with reference to the implantable device of FIG. 1.

In some embodiments, driving the implantable device into the bladder in block 3206 includes observing the implantable device in the bladder to ensure the device was properly implanted. For example, the device may be observed using a cystoscope, ultrasound, or x-ray.

In some embodiments, driving the implantable device into the bladder in block 3206 further includes introducing a volume of fluid into the bladder before the device is driven into the bladder. The fluid may be, for example, water or saline. The fluid may serve as a cushion in the bladder, reducing the likelihood of the implantable device contacting the posterior of the bladder upon implantation, which may cause discomfort or bladder perforation.

In block 3208, the deployment instrument is removed from the body. If a stylet was employed in block 3206 to drive the implantable device into the bladder, the stylet is also removed. The stylet can be removed be either before or simultaneously with the deployment instrument. Thereafter, in block 3210, the implantable device remains implanted in the body for a period, such as a period of hours, days, weeks, or even months. In embodiments in which the implanted device is a drug delivery device, the device remains implanted in the body in block 3210 to release a drug into the body, such as to release drug from the device into the bladder and to the urothelial tissues and other local or regional tissues.

In some embodiments, the method includes removing the implantable device from the body in block 3212. Removing the device from the body may include inserting a removal instrument into the body, locating the implanted device in the body, and pulling the implanted device through from the body through the removal instrument. For example, the removal instrument may be a cystoscope or catheter that is inserted through the urethra until its distal end reaches the bladder.

Once the removal instrument is positioned in the body, the implanted device may be located in the body and is pulled into the removal instrument. For example, forceps passed through the removal instrument may be used to locate the implanted device and to pull the device into the removal instrument. The device may fold upon itself or assume the deployment shape as it enters the removal instrument. In embodiments in which the device is an implantable drug delivery device, a drug reservoir portion of the device may be at least partially depleted or empty upon removal, facilitating removal. In some embodiments, the device may be located and pulled into the removal instrument using a retrieval feature. For example, the device may include a magnetized portion that is drawn to a magnetized portion of the removal instrument and/or a magnetized portion of the forceps, facilitating retrieval. In other embodiments, the implantable device may include a string that is grasped to pull the implantable device into the removal instrument.

Once the implantable device is located, the implantable device may be pulled through the removal instrument, and thereafter the removal instrument may be removed from the body. Alternatively, the implantable device and removal instrument may be removed from the body simultaneously.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method for deploying an implantable device into an implantation site, the method comprising:
   inserting a deployment instrument into a natural lumen of the body to reach the implantation site, wherein the deployment instrument comprises a reinforced tip;
   introducing the implantable device into the deployment instrument; and
   driving the implantable device through the deployment instrument using a stylet, the stylet comprising a central body portion and a distal tip portion, the central body portion having a smaller cross-sectional area than an inner lumen of the deployment instrument, and the distal tip portion having a cross-sectional area that is about the same as the inner lumen of the deployment instrument.

2. The method of claim 1, wherein introducing the implantable device into the deployment instrument comprises preloading the implantable device into the deployment instrument before the deployment instrument is inserted into the natural lumen.

3. The method of claim 1, wherein introducing the implantable device into the deployment instrument comprises loading the implantable device into a proximal end of the deployment instrument after the deployment instrument is inserted into the natural lumen.

4. The method of claim 1, further comprising permitting fluid to return through the deployment instrument to verify placement of a distal end of the deployment instrument at the implantation site.

5. The method of claim 4, further comprising preventing the return of fluid through the deployment instrument once placement of the distal end of the deployment instrument at the implantation site is verified.

6. The method of claim 1, wherein the deployment instrument comprises a reinforced coude tip and a substantially solid, rounded distal end.

7. The method of claim 1, wherein the deployment instrument comprises an exit opening formed through a side of the deployment instrument, wherein the inner lumen curves to terminate at the exit opening, and wherein driving the implantable device through the deployment instrument comprises pushing the implantable device out of the exit opening using the stylet.

8. The method of claim 1, further comprising injecting a stream of fluid into the deployment instrument.

9. The method of claim 8, wherein injecting the stream of fluid into the deployment instrument comprises injecting the stream of fluid through an internal lumen of the stylet and into an internal lumen of the deployment instrument.

10. A method of delivering an implantable device through the urethra and into the bladder, the method comprising:
- inserting a deployment instrument into the urethra;
- inserting the implantable device into the deployment instrument;
- driving the implantable device through the deployment instrument and into the bladder by a combination of injecting a stream of fluid into the deployment instrument and pushing the implantable device with a stylet; and
- removing the deployment instrument from the urethra, leaving the implantable device implanted in the bladder.

11. The method of claim 10, wherein inserting the implantable device into the deployment instrument comprises pre-loading the implantable device into the deployment instrument before the deployment instrument is inserted into the urethra.

12. The method of claim 10, wherein inserting the implantable device into the deployment instrument comprises loading the implantable device into a proximal end of the deployment instrument after the deployment instrument is inserted into the urethra.

13. The method of claim 10, further comprising delivering a volume of fluid through the deployment instrument into the bladder before the implantable device is implanted to form a cushion for the implantable device.

14. The method of claim 10, wherein injecting the stream of fluid into the deployment instrument comprises injecting a fluid that has an equal or higher viscosity than water.

15. The method of claim 10, wherein injecting the stream of fluid into the deployment instrument comprises injecting a stream of liquid lubricant into the deployment instrument.

16. The method of claim 10, further comprising inflating an inflatable balloon on a distal end of the deployment instrument to anchor the distal end in the bladder.

17. The method of claim 10, further comprising permitting urine to return through the deployment instrument to verify placement of a distal end of the deployment instrument in the bladder.

18. The method of claim 17, further comprising preventing the return of urine through the deployment instrument once placement of the distal end of the deployment instrument in the bladder is verified.

19. The method of claim 10, wherein the stream of fluid acts on a movable seal positioned upstream of the implantable device, the movable seal acting on the implantable device to drive the implantable device through the deployment instrument.

20. The method of claim 10, wherein driving the implantable device through the deployment instrument and into the bladder comprises pushing the implantable device with the stylet after injecting the stream of fluid into the deployment instrument.

21. The method of claim 10, wherein injecting the stream of fluid into the deployment instrument comprises injecting the stream of fluid through an internal lumen of the stylet and into an internal lumen of the deployment instrument.

\* \* \* \* \*